(12) United States Patent
Han et al.

(10) Patent No.: US 6,444,811 B1
(45) Date of Patent: Sep. 3, 2002

(54) PYRAZINONES, COMPOSITIONS CONTAINING SUCH COMPOUNDS AND METHODS OF USE

(75) Inventors: Yongxin Han, Kirkland; Andre Giroux, Ste-Anne-De-Bellevue; Robert Zamboni, Pointe Claire; Daniel J. McKay, Ottawa; Christopher I. Bayly, Beaconsfield; Erich L. Grimm, Baie d'Urfe; John Colucci, Westmount, all of (CA)

(73) Assignee: Merck Frosst Canada & Co., Nova Scotia (CA)

( * ) Notice: Subject to any disclaimer, the term of this patent is extended or adjusted under 35 U.S.C. 154(b) by 0 days.

(21) Appl. No.: 09/618,875

(22) Filed: Jul. 19, 2000

Related U.S. Application Data

(60) Provisional application No. 60/144,466, filed on Jul. 19, 1999, and provisional application No. 60/170,614, filed on Dec. 14, 1999.

(51) Int. Cl.[7] .................... C07D 413/12; C07D 413/14; C07D 417/12; C07D 417/14; C07D 241/20
(52) U.S. Cl. .................. 544/42; 544/349; 544/357; 544/405; 544/408; 514/235.8; 514/249; 514/252.11; 514/255.05; 514/25.06
(58) Field of Search .................... 544/120, 349, 544/357, 405, 408; 514/235.8, 249, 252.11

(56) References Cited

U.S. PATENT DOCUMENTS

| 5,866,573 A | 2/1999 | Sanderson et al. |
| 5,981,546 A | * 11/1999 | Duggan et al. ............. 514/300 |

FOREIGN PATENT DOCUMENTS

| WO | WO98/08840 | 3/1998 |
| WO | WO98/42342 | 10/1998 |
| WO | WO98/09949 | 12/1998 |
| WO | WO99/11267 | 3/1999 |
| WO | WO97/40024 | 10/2000 |

OTHER PUBLICATIONS

Talanian et al., Annual Reports in Medicinal Chemistry, vol. 33, pp. 273–282, 1998.*
Sanderson, et al., J. Med Chem, 1998, 41, 4466–4474–Efficacious, Orally Bioavailable Thrombin Inhibitors Based on 3–Aminopyridinone or 3–Aminopyrazinone acetamide Peptidominetic Templates.

* cited by examiner

*Primary Examiner*—Emily Bernhardt
(74) *Attorney, Agent, or Firm*—Raynard Yuro; David L. Rose

(57) ABSTRACT

Compounds represented by formula I:

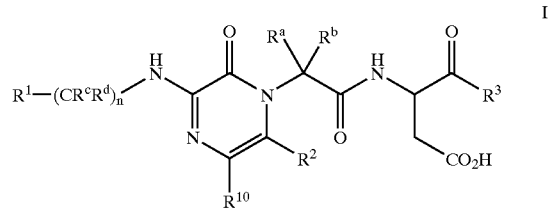

as well as pharmaceutically acceptable salts, esters, N-oxides and hydrates thereof are disclosed. Pharmaceutical compositions and methods of use are also included. The compounds are active against the caspase-3 enzyme, and thus are useful to treat fin caspase-3 mediated diseases and conditions.

1 Claim, No Drawings

PYRAZINONES, COMPOSITIONS CONTAINING SUCH COMPOUNDS AND METHODS OF USE

CROSS-REFERENCE TO RELATED APPLICATIONS

This application is a non-provisional application related to U.S. application Ser. No.60/144,466, filed on Jul. 19, 1999 and Ser. No. 60/170,614, file on Dec. 14, 1999 priority of which is claimed hereunder.

BACKGROUND OF THE INVENTION

Apoptotic cell suicide is a fundamentally important biological process that is required to maintain the integrity and homeostasis of multicellular organisms. Inappropriate apoptosis, however, underlies the etiology of many of the most intractable of human diseases. In only the last few years, many of the molecules that participate in a conserved biochemical pathway that mediates the highly ordered process of apoptotic cell suicide have been identified. At the heart of this pathway are a family of cysteine proteases, the 'caspases', that are related to mammalian interleukin-1β converting enzyme (ICE/caspase-1) and to CED-3, the product of a gene that is necessary for apoptotic suicide in the nematode *C. elegans* (Nicholson et al., 1997, Trends Biochem Sci 22:299–306). The role of these proteases in dell suicide is to disable critical homeostatic and repair processes as well as to cleave key structural components, resulting in the systematic and orderly disassembly of the dying cell.

The central importance of caspases in these processes has been demonstrated with both macromolecular and peptide-based inhibitors (which prevent apoptosis from occurring in vitro and in vivo) as well as by genetic approaches. Inhibition of apoptosis via attenuation of caspase activity should therefore be useful in the treatment of human diseases where inappropriate apoptosis is prominent or contributes to disease pathogenesis. Caspase inhibitors would thus be useful for the treatment of human diseases including, but not limited to, acute disorders such as cardiac and cerebral ischemia/reperfusion injury (e.g. stroke), spinal cord injury and organ damage during transplantation, sepsis, bacterial meningitis, chronic disorders such as neurodegenerative diseases (e.g. Alzheimer's, polyglutamine-repeat disorders, Down's, spinal muscular atrophy, multiple sclerosis), immunodeficiency (e.g. HIV), diabetes, alopecia and aging.

Thirteen caspases have so far been identified in human cells. Each is synthesized as a catalytically dormant proenzyme containing an amino-terminal pro-domain followed by the large and small subunits of the heterodimeric active enzyme. The subunits are excised from the proenzyme by cleavage at Asp-X junctions (Nicholson et al., 1997, Trends Biochem Sci 22:299–306). The strict requirement by caspases for Asp in the P1 position of substrates is consistent with a mechanism whereby proenzyme maturation can be either autocatalytic or performed by other caspases. The three dimensional crystal structures of mature caspase-1 and -3 show that the large subunit contains the principle components of the catalytic machinery, including the active site Cys residue which is harbored within the conserved pentapeptide motif, QACxG, and residues that stabilize the oxyanion of the tetrahedral transition state (Wilson et al., 1994, Nature 370:270–75; Walker et al., 1994, Cell 78:342–52;.Rotonda et al., 1996, Nat Struct Biol 3:619–25). Both subunits contribute residues which stabilize the P1 Asp of substrates while the small subunit appears to contain most of the determinants that dictate substrate specificity and, in particular, those which form the specificity-determining S4 subsite. One distinctive feature of these proteases is the absolute requirement for an aspartic acid residue in the substrate P1 position. The carboxylate side chain of the substrate P1 Asp is tethered by four residues in caspase-1 (Arg179, Gln238 from p20 and Arg341, Ser347 from p10) that are absolutely conserved in all caspase family members. Catalysis involves a typical cysteine protease mechanism involving a catalytic dyad, composed of His237 and Cys285 (contained within an absolutely conserved QACxG pentapeptide) and an 'oxyanion hole' involving Gly238 and Cys285. Inhibitors bind, however, in an unexpected non-transition state configuration (which raises important considerations for inhibitor design) with the oxyanion of the thiohemiacetal being stabilized by the active site His237.

Members of the caspase family can be divided into three functional subgroups based on their substrate specificities which have been defined by a positional-scanning combinatorial substrate approach. The principle effectors of apoptosis (group II caspases, which include caspases-2, -3 and -7 as well as *C. elegans* CED-3) have specificity for [P4] DExD[P1], a motif found at the cleavage site of most proteins known to be cleaved during apoptosis. On the other hand, the specificity of group III caspases (caspases-6, -8, -9 and -10, as well as CTL-derived granzyme B) is [P4](I,V,L)ExD[P1] which corresponds to the activation site at the junction between the large and small subunits of other caspase proenzymes including group II (effector) family members. This and other evidence indicates that group III caspases function as upstream activators of group II caspases in a proteolytic cascade that amplifies the death signal. The role of group I caspases (caspases-1, -4 and -5) appears to be to mediate cytokine maturation and their role in apoptosis, if any, has not been substantiated.

A tetrapeptide corresponding to the substrate P4-P1 residues is sufficient for specific recognition by caspases and as a consequence has formed the basis for inhibitor design. In addition to the requirement for a P1 Asp, the P4 residue in particular appears to be most important for substrate recognition and specificity. Caspase-1, for example, prefers a hydrophobic residue such as Tyr in P4 (which corresponds to its YVHD cleavage site within proIL-1β) whereas caspase-3 (and other group II enzymes) has. a preference for an anionic Asp residue (which corresponds to the DXXD cleavage sites within most polypeptides that are cleaved by these enzymes during apoptosis). Peptide aldehydes, nitriles and ketones are potent reversible inhibitors of these proteases while compounds that form thiomethylketone adducts with the active site cysteine (e.g. peptide (acyloxy) methylketones) are potent irreversible inhibitors. For example, the tetrapeptide aldehyde Ac-YVAD-CHO (which was designed to mimic the YVHD caspase-1 recognition sequence within proIL-1β) is a potent inhibitor of caspase-1 (Ki<1 nM) but a poor inhibitor of caspase-3 (Ki=12 $\mu$M) (Thomberry et al., 1992, Nature 356:768–74). In contrast, the Ac-DEVD-CHO tetrapeptide aldehyde (which was designed to mimic the caspase-3 recognition site) is a very potent inhibitor of caspase-3 (Ki<1 nM) although it is also a weaker but reasonable inhibitor of caspase-1, presumably owing to promiscuity in the S4 subsite of this enzyme (Nicholson et al., 1995, Nature 376:37–43).

Several features plague these peptide-derived inhibitors as a platform for drug design. In addition to their poor metabolic stability and poor membrane permeability, the slow-binding time-dependent inhibition of activity (e.g. kon caspase-1:Ac-YVAD-CHO=3.8×10$^5$ M-1s-1; kon caspase-3:Ac-DEVD-CHO=1.3×10$^5$ M-1s-1) precludes them from the rapid inhibition characteristics that may be necessary to abolish enzymatic activity in vivo. The present invention describes the resolution of these issues with the discovery of a novel series of non-peptidyl caspase inhibitors containing a pyrazinone core.

SUMMARY OF THE INVENTION

A compound represented by formula I:

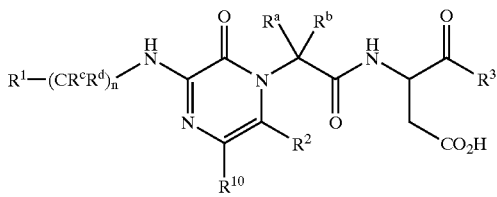

or a pharmaceutically acceptable salt, ester, N-oxide or hydrate thereof wherein:

$R^1$ is selected from the group consisting of: OH, $C_{1-6}$alkyl, HET, Aryl, $C_{1-6}$alkoxy, $NH_2$, $NHC_{1-6}$alkyl, $N(C_{1-6}$alkyl$)_2$, $C_{1-6}$ alkylC(O), $C_{1-6}$ alkylS(O)$_y$, Aryl-S(O)$_y$, HET-S(O)$_y$ wherein y is 0, 1 or 2, Aryl-C(O) and HET-C(O), the alkyl and alkyl portions of which being optionally substituted with 1–2 members selected from the group consisting of: OH, Aryl$^1$, HET, halo, $NH_2$, $NHCH_3$, $N(CH_3)_2$, $CO_2H$, $CF_3$ and $C_{1-4}$-acyl;

Aryl represents a $C_{6-14}$aromatic 1–3 ring system optionally substituted with 1–3 members selected from OH, $C_{1-6}$ alkyl, $OC_{1-6}$ alkyl, Aryl$^1$, HET, halo, $NH_2$, $NHCH_3$, $N(CH_3)_2$, $CF_3$, $CO_2H$ and $C_{1-4}$acyl;

Aryl$^1$ represents a $C_{6-14}$ membered aromatic ring system having 1–3 rings and optionally substituted with 1–3 members selected from the group consisting of: OH, HET, halo, $NH_2$, $NHCH_3$, $N(CH_3)_2$, $CO_2H$ and $C_{1-4}$-acyl;

HET represents a 5 to 15 membered aromatic, partially aromatic or non-aromatic ring system, containing 1–4 heteroatoms selected from O, S and N, and optionally substituted with 1–2 oxo groups and 1–3 groups selected from halo, $C_{1-4}$alkyl, $C_{1-4}$alkoxy, $CF_3$ and $C_{1-4}$acyl;

$R^a$ and $R^b$ independently represent a member selected from the group consisting of: H, Aryl, $C_{1-6}$alkyl optionally substituted by 1–3 of halo, $OR^4$, $SR^4$ and $C_{5-7}$cycloalkyl optionally containing one heteroatom selected from O, S and $NR_5$, or in the alternative, $R^a$ and $R^b$ are taken in combination and represent a non-aromatic carbocyclic 4–7 membered ring, optionally containing one heteroatom selected from O, S and $NR^5$;

$R^4$ is selected from the group consisting of: H, $C_{1-5}$alkyl, Aryl and Aryl-$C_{1-4}$alkyl optionally substituted with 1–2 groups selected from halo and $C_{1-4}$alkyl;

$R^5$ is H, $C_{1-4}$alkyl or $C_{1-4}$acyl;

$R^c$ and $R^d$ each independently represents a member selected from the group consisting of: H, $C_{1-6}$alkyl and Aryl, or in the alternative, $R^c$ and $R^d$ are taken in combination and represent a non-aromatic carbocyclic ring of 3–7 members, optionally containing one heteroatom selected from O, S and $NR^5$;

n is an integer from 0–6 inclusive;

$R^2$ represents H, halo or $C_{1-6}$alkyl;

$R^3$ represents H, $C_{1-6}$alkyl, Aryl, HET $C_{1-6}$alkylSR$^6$, $C_{1-6}$alkylOR$^6$, $C_{1-6}$alkylOC(O)R$^7$ or $C_{1-6}$alkylNR$^8$R$^9$;

$R^6$ represents $C_{1-6}$alkyl, Aryl, HET or Aryl-$C_{1-6}$alkyl, said alkyl and the alkyl portions being optionally substituted with 1–3 members selected from the group consisting of: OH, halo, $NH_2$, $NHCH_3$, $N(CH_3)_2$, $CO_2H$, $CF_3$ and $C_{1-4}$ acyl;

$R^7$ represents $C_{1-8}$alkyl, Aryl or HET;

$R^8$ and $R^9$ independently represent H, $C_{1-10}$alklyl, Aryl, HET, $C_{1-6}$alkylN($C_{1-6}$alkyl$)_{0-2}$, Aryl-$C_{1-6}$alkyl, $C_{1-6}$alkylOH, or $C_{1-6}$alkylOC$_{1-6}$alkyl , or $R^8$ $R^9$ are taken in combination with the nitrogen atom to which they are attached and represent a 3–10 membered ring system containing 1–4 hetero atoms selected from O, S, N and optionally substituted with 1–2 oxo groups, and 1–3 groups selected from $C_{1-6}$alkyl, HET, $CO_2R^c$ and $C(O)N(R^c)_2$, said alkyl and alkyl portions being optionally substituted with 1–3 groups selected from halo, $C_{1-3}$alkyl, hydroxy$C_{1-3}$ alkyl, $C_{1-3}$alkoxy, $C_{1-3}$alkoxy$C_{1-3}$alkyl and Aryl$^1$, and $R^{10}$ represents H, $C_{1-20}$ alkyl, aryl or HET, with aryl and HET as previously described.

The invention also encompasses a pharmaceutical composition comprising a compound of formula I in combination with a pharmaceutically acceptable carrier.

DETAILED DESCRIPTION OF THE INVENTION

The present invention relates to a compound represented by formula I:

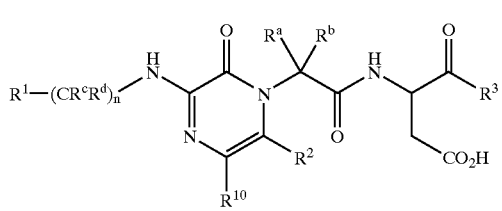

or a pharmaceutically acceptable salt, ester, N-oxide or hydrate thereof wherein:

$R^1$ is selected from the group consisting of: OH, $C_{1-6}$alkyl, HET, Aryl, $C_{1-6}$alkoxy, $NH_2$, $NHC_{1-6}$alkyl, $N(C_{1-6}$ alkyl$)_2$, $C_{1-6}$ alkylC(O), $C_{1-6}$ alkylS(O)$_y$, Aryl-S(O)$_y$, HET-S(O)$_y$ wherein y is 0, 1 or 2, Aryl-C(O) and HET-C(O), the alkyl and alkyl portions of which being optionally substituted with 1–2 members selected from the group consisting of: OH, Aryl$^1$, HET, halo, $NH_2$, $NHCH_3$, $N(CH_3)_2$, $CO_2H$, $CF_3$ and $C_{1-4}$-acyl;

Aryl represents a $C_{6-14}$aromatic 1–3 ring system optionally substituted with 1–3 members selected from OH, $C_{1-6}$ alkyl, $OC_{1-6}$ alkyl, Aryl$^1$, HET, halo, $NH_2$, $NHCH_3$, $N(CH_3)_2$, $CF_3$, $CO_2H$ and $C_{1-4}$acyl;

Aryl$^1$ represents a $C_{6-14}$ membered aromatic ring system having 1–3 rings and optionally substituted with 1–3 members selected from the group consisting of: OH, HET, halo, $NH_2$, $NHCH_3$, $N(CH_3)_2$, $CO_2H$ and $C_{1-4}$-acyl;

HET represents a 5 to 15 membered aromatic, partially aromatic or non-aromatic ring system, containing 1–4 heteroatoms selected from O, S and N, and optionally substituted with 1–2 oxo groups and 1–3 groups selected from halo, $C_{1-4}$alkyl, $C_{1-4}$alkoxy, $CF_3$ and $C_{1-4}$acyl;

$R^a$ and $R^b$ independently represent a member selected from the group consisting of: H, Aryl, $C_{1-6}$alkyl optionally substituted by 1–3 of halo, $OR^4$, $SR^4$ and $C_{5-7}$cycloalkyl optionally containing one heteroatom selected from O, S and $NR_5$, or in the alternative, $R^a$ and $R^b$ are taken in combination and represent a non-aromatic carbocyclic 4–7 membered ring, optionally containing one heteroatom selected from O, S and $NR^5$;

$R^4$ is selected from the group consisting of: H, $C_{1-5}$alkyl, Aryl and Aryl-$C_{1-4}$alkyl optionally substituted with 1–2 groups selected from halo and $C_{1-4}$alkyl;

$R^5$ is H or $C_{1-4}$alkyl;

$R^c$ and $R^d$ each independently represents a member selected from the group consisting of: H, $C_{1-6}$alkyl and Aryl, or in the alternative, $R^c$ and $R^d$ are taken in combination and represent a non-aromatic carbocyclic ring of 3–7 members, optionally containing one heteroatom selected from O, S and $NR^5$;

n is an integer from 0–6 inclusive;

$R^2$ represents H, halo or $C_{1-6}$alkyl;

$R^3$ represents H, $C_{1-6}$alkyl, Aryl, HET, $C_{1-6}$alkyl$SR^6$, $C_{1-6}$alkyl$OR^6$, $C_{1-6}$alkyl$OC(O)R^7$ or $C_{1-6}$alkyl$NR^8R^9$;

$R^6$ represents $C_{1-6}$alkyl, Aryl, HET or Aryl-$C_{1-6}$alkyl, said alkyl and the alkyl portions being optionally substituted with 1–3 members selected from the group consisting of: OH, halo, $NH_2$, $NHCH_3$, $N(CH_3)_2$, $CO_2H$, $CF_3$ and $C_{1-4}$ acyl;

$R^7$ represents $C_{1-8}$alkyl, Aryl or HET;

$R^8$ and $R^9$ independently represent H, $C_{1-10}$alkyl, Aryl, HET, $C_{1-6}$alkyl$N(C_{1-6}$alkyl$)_{0-2}$, Aryl-$C_{1-6}$alkyl, $C_{1-6}$alkyl$OH$, or $C_{1-6}$alkyl$OC_{1-6}$alkyl, or $R^8$ and $R^9$ are taken in combination with the nitrogen atom to which they are attached and represent a 3–10 membered ring system containing 1–4 heteroatoms selected from O, S, N and optionally substituted with 1–2 oxo groups, and 1–3 groups selected from $C_{1-6}$alkyl, HET, $CO_2R^c$ and $C(O)N(R^c)_2$, said alkyl and alkyl portions being optionally substituted with 1–3 groups selected from halo, $C_{1-3}$alkyl, hydroxy$C_{1-3}$ alkyl, $C_{1-3}$alkoxy, $C_{1-3}$alkoxy$C_{1-3}$alkyl and $Aryl^1$, and $R^{10}$ represents H, $C_{1-20}$ alkyl, aryl or HET, with aryl and HET as previously described.

More particularly, the present invention relates to a compound represented by formula I':

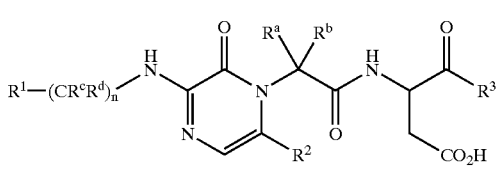

I' or a pharmaceutically acceptable salt, ester, N-oxide or hydrate thereof wherein:

$R^1$ is selected from the group consisting of: OH, $C_{1-6}$alkyl, HET, Aryl, $C_{1-6}$alkoxy, $NH_2$, $NHC_{1-6}$alkyl, $N(C_{1-6}$ alkyl$)_2$, $C_{1-6}$ alkyl$C(O)$, $C_{1-6}$ alkyl$S(O)_y$, Aryl-$S(O)_y$, HET-$S(O)_y$ wherein y is 0, 1 or 2, Aryl-$C(O)$ and HET-$C(O)$, the alkyl and alkyl portions of which being optionally substituted with 1–2 members selected from the group consisting of: OH, $Aryl^1$, HET, halo, $NH_2$, $NHCH_3$, $N(CH_3)_2$, $CO_2H$, $CF_3$ and $C_{1-4}$-acyl;

Aryl represents a $C_{6-14}$aromatic 1–3 ring system optionally substituted with 1–3 members selected from OH, $C_{1-6}$ alkyl, $OC_{1-6}$ alkyl, $Aryl^1$, HET, halo, $NH_2$, $NHCH_3$, $N(CH_3)_2$, $CF_3$, $CO_2H$ and $C_{1-4}$acyl;

$Aryl^1$ represents a $C_{6-14}$ membered aromatic ring system having 1–3 rings and optionally substituted with 1–3 members selected from the group consisting of: OH, HET, halo, $NH_2$, $NHCH_3$, $N(CH_3)_2$, $CO_2H$ and $C_{1-4}$-acyl;

HET represents a 5 to 15 membered aromatic, partially aromatic or non-aromatic ring system, containing 1–4 heteroatoms selected from O, S and N, and optionally substituted with 1–2 oxo groups and 1–3 groups selected from halo, $C_{1-4}$alkyl, $C_{1-4}$alkoxy, $CF_3$ and $C_{1-4}$acyl;

$R^a$ and $R^b$ independently represent a member selected from the group consisting of: H, Aryl, $C_{1-6}$alkyl optionally substituted by 1–3 of halo, $OR^4$, $SR^4$ and $C_{5-7}$cycloalkyl optionally containing one heteroatom selected from O, S and $NR_5$, or in the alternative, $R^a$ and $R^b$ are taken in combination and represent a non-aromatic carbocyclic 4–7 membered ring, optionally containing one heteroatom selected from O, S and $NR^5$;

$R^4$ is selected from the group consisting of: H, $C_{1-5}$alkyl, Aryl and Aryl-$C_{1-4}$alkyl optionally substituted with 1–2 groups selected from halo and $C_{1-4}$alkyl;

$R^5$ is H or $C_{1-4}$alkyl;

$R^c$ and $R^d$ each independently represents a member selected from the group consisting of: H, $C_{1-6}$alkyl and Aryl, or in the alternative, $R^c$ and $R^d$ are taken in combination and represent a non-aromatic carbocyclic ring of 3–7 members, optionally containing one heteroatom selected from O, S and $NR^5$;

n is an integer from 0–6 inclusive;

$R^2$ represents H, halo or $C_{1-6}$alkyl;

$R^3$ represents H, $C_{1-6}$alkyl, Aryl, HET, $C_{1-6}$alkyl$SR^6$, $C_{1-6}$alkyl$OR^6$, $C_{1-6}$alkyl$OC(O)R^7$ or $C_{1-6}$alkyl$NR^8R^9$;

$R^6$ represents $C_{1-6}$alkyl, Aryl, HET or Aryl-$C_{1-6}$alkyl, said alkyl and the alkyl portions being optionally substituted with 1–3 members selected from the group consisting of: OH, halo, $NH_2$, $NHCH_3$, $N(CH_3)_2$, $CO_2H$, $CF_3$ and $C_{1-4}$ acyl;

$R^7$ represents $C_{1-8}$alkyl, Aryl or HET;

$R^8$ and $R^9$ independently represent H, $C_{1-10}$alkyl, Aryl, HET, $C_{1-6}$alkyl$N(C_{1-6}$alkyl$)_{0-2}$, Aryl-$C_{1-6}$alkyl, $C_{1-6}$alkyl OH, or $C_{1-6}$alkyl$C_{1-6}$alkyl, or $R^8$ and $R^9$ are taken in combination with the nitrogen atom to which they are attached and represent a 3–10 membered ring system containing 1–4 heteroatoms selected from O, S, N and optionally substituted with 1–2 oxo groups, and 1–3 groups selected from $C_{1-6}$alkyl, HET, $CO_2R^c$ and $C(O)N(R^c)_2$, said alkyl and alkyl portions being optionally substituted with 1–3 groups selected from halo, $C_{1-3}$alkyl, hydroxy$C_{1-3}$alkyl, $C_{1-3}$alkoxy, $C_{1-3}$alkoxy$C_{1-3}$alkyl and $Aryl^1$.

The invention also encompasses a pharmaceutical composition comprising a compound of formula I in combination with a pharmaceutically acceptable carrier.

The invention also encompasses a method of treating cardiac and cerebral ischemia/reperfusion injury (e.g.

stroke), type I diabetes, immune deficiency syndrome (including AIDS), cerebral and spinal cord trauma injury, organ damage during transplantation, alopecia, sepsis, bacterial meningitis, aging, Parkinson's disease, Alzheimer's disease, Down's syndrome, spinal muscular atrophy, multiple sclerosis and neurodegenerative disorders, comprising administering to a mammalian patient in need of such treatment an effective amount of a compound of formula I.

Alkyl as used herein means linear, branched or cyclic structures and combinations thereof, containing one to twenty carbon atoms unless otherwise specified. Examples of alkyl groups include methyl, ethyl, propyl, isopropyl, butyl, s- and t-butyl, pentyl, hexyl, heptyl, octyl, nonyl, undecyl, dodecyl, tridecyl, tetradecyl, pentadecyl, eicosyl, 3,7-diethyl-2,2-dimethyl-4-propylnonyl, cyclopropyl, cyclopentyl, cycloheptyl, adamantyl, cyclododecylmethyl, 2-ethyl-1-bicyclo[4.4.0]decyl and the like.

Alkylcarbonyl signifies groups having the formula —C(O)-alkyl, wherein alkyl is defined as above.

Alkylsulfonyl signifies groups having the formula —S(O)$_2$-alkyl, wherein alkyl is defined as above.

Fluoroalkyl means linear, branched or cyclic alkyl groups and combinations thereof, of one to ten carbon atoms, in which one or more hydrogen but no more than six is replaced by fluorine. Examples are —CF$_3$, —CH$_2$CH2F, and —CH$_2$CF$_3$ and the like.

Alkoxy means alkoxy groups of one to ten carbon atoms of a straight, branched or cyclic configuration. Examples of alkoxy groups include methoxy, ethoxy, propoxy, isopropoxy, and the like.

Alkoxycarbonyl signifies groups having the formula —C(O)-alkoxy, wherein alkoxy is defined as above.

Alkylthio means alkylthio groups of one to ten carbon atoms of a straight, branched or cyclic configuration. Examples of alkylthio groups include methylthio, propylthio, isopropylthio, etc. By way of illustration, the propylthio group signifies —SCH$_2$CH$_2$CH$_3$.

Aryl is a 1–3 ring aromatic group containing 6–14 carbon atoms. Examples include phenyl, naphthyl, phenanthrenyl and the like. Ring system refers to single rings as well as 2–4 rings that are fused.

HET represents a 5 to 15 membered aromatic, partially aromatic or non-aromatic ring system, containing 1–4 heteroatoms selected from O, S and N, and optionally substituted with 1–2 oxo groups and 1–3 groups selected from halo, C$_{1-4}$alkyl, C$_{1-4}$alkoxy, CF$_3$ and C$_{1-4}$acyl. HET thus includes heteroaryl and heterocyclyl.

Heteroaryl is a heteroaromatic 5–15 membered group containing at least one heteroatom selected from O, S and N with up to 4 such heteroatoms being present in the ring system, e.g., pyridyl, furyl, thienyl, thiazolyl, isothiazolyl, imidazolyl, benzimidazolyl, pyrazinyl, pyrimidyl, quinolyl, isoquinolyl, benzofuryl, benzothienyl, pyrazolyl, indolyl, purinyl, isoxazolyl, oxazolyl, coumarinyl, benzocoumarinyl and the like.

Halo includes F, Cl, Br and I.

N-oxide refers to oxides of the N atoms in the HET groups.

For purposes of this specification, the following abbreviations have the indicated meanings:
AcOH=acetic acid
Alloc=allyloxycarbonyl
APCI=atmospheric pressure chemical ionization
BOC=t-butyloxycarbonyl
CBZ=carbobenzoxy
DCC=1,3-dicyclohexylcarbodiimide
DIBAL diisobutyl aluminum hydride
DIEA=N,N-diisoproylethylamine
DMAP=4-(dimethylamino)pyridine
EDCI=1-(3-dimethylaminopropyl)-3-ethylcarbodiimide hydrochloride
EDTA=ethylenediaminetetraacetic acid, tetrasodium salt hydrate
ESI=electrospray ionization
FAB=fast atom bombardment
FMOC=9-fluorenylmethoxycarbonyl
HMPA=hexamethylphosphoramide
HATU=O-(7-Azabenzotriazol-1-yl)N,N,N',N'-tetramethyluronium hexafluorophosphate
HOBt=1-hydroxybenzotriazole
HRMS=high resolution mass spectrometry
ICI=iodine monochloride
IBCF=isobutyl chloroformate
KHMDS potassium hexamethyldisilazane
LDA=lithium diisopropylamide
MCPBA=metachloroperbenzoic acid
Ms=methanesulfonyl=mesyl
MsO=methanesulfonate=mesylate
NBS=N-bromosuccinimide
NMM=4-methylmorpholine
PCC=pyridinium chlorochromate
PDC=pyridinium dichromate
Ph=phenyl
PPTS=pyridinium p-toluene sulfonate
pTSA=p-toluene sulfonic acid
r.t.=room temperature
rac.=racemic
TfO=trifluoromethanesulfonate=triflate
TLC=thin layer chromatography
Alkyl Group Abbreviations
Me=methyl
Et=ethyl
n-Pr=normal propyl
i-Pr=isopropyl
n-Bu=normal butyl
i-Bu=isobutyl
s-Bu=secondary butyl
t-Bu=tertiary butyl One subgroup of compounds that is of particular interest relates to compounds of formula I wherein $R^1$ represents HET or Aryl, said HET representing a 5 to 15 membered aromatic, partially aromatic or non-aromatic ring or ring system, containing from 1–4 heteroatoms selected from O, S and N, and optionally substituted with 1–2 groups selected from oxo, halo, C$_{1-4}$alkyl, C$_{1-4}$alkoxy and C$_{1-4}$acyl, and said Aryl being selected from phenyl and naphthyl, and being optionally substituted with 1–3 members selected from the group consisting of: OH, Aryl$^1$, HET, halo, NH$_2$, NHCH$_3$, N(CH$_3$)$_2$, CO$_2$H and C$_{1-4}$-acyl. Within this subset of compounds, all other variables are as originally defined.

More particularly, a subgroup that is of interest relates to compounds of formula I wherein $R^1$ represents HET optionally substituted with 1–2 groups selected from oxo, halo, C$_{1-4}$alkyl, C$_{1-4}$alkoxy and C$_{1-4}$acyl. Within this subset of compounds, all other variables are as originally defined.

Even more particularly, a subgroup that is of interest relates to compounds of formula I wherein $R^1$ represents HET substituted with 1–2 groups selected from oxo, halo, C$_{1-4}$alkyl, C$_{1-4}$alkoxy and C$_{1-4}$acyl. Within this subset of compounds, all other variables are as originally defined.

Even more particularly, a subgroup that is of interest relates to compounds of formula I wherein $R^1$ represents HET selected from the group consisting of: pyridinyl, pyrazinyl, pyrrolyl, furanyl, pyrazolyl, imidazolyl, benzimidazolyl, oxathiazolyl, thiazolyl, benzothiazolyl, oxazolyl, pyrrazolyl, 1,2-diazolyl, 1,2,3- and 1,2,4-triazolyl, 1,2,4- and 1,2,5-oxadiazolyl, 1,2,4- and 1,2,5-thiadiazolyl, tetrazolyl, isoxazolyl, thienyl, azepinyl, pyrrolidinyl, piperidinyl, piperazinyl, optionally substituted with 1–2 groups selected from halo, $C_{1-4}$alkyl and $C_{1-4}$alkoxy. Within this subset of compounds, all other variables are as originally defined.

Another group of compounds that is of particular interest relates to compounds of formula I wherein $R^1$ represents Aryl said Aryl being phenyl optionally substituted with 1–3 members selected from the group consisting of: OH, Aryl$^1$, HET, halo, $NH_2$, $NHCH_3$, $N(CH_3)_2$, $CO_2H$ and $C_{1-4}$-acyl. Within this subset of compounds, all other variables are as originally defined.

Another group of compounds that is particular interest relates to compounds of formula I wherein $R^c$ and $R^d$ represent H, and n is an integer of from 0–3 inclusive. In particular, $(R^cR^d)_n$ represents methylene, ethylene or propylene.

Another group of compounds that is particular interest relates to compounds of formula I wherein $R^a$ and $R^b$ independently represent H or $C_{1-6}$alkyl, optionally substituted with halo, $OR^4$, $SR^4$ or $C_{5-7}$cycloalkyl optionally containing one heteroatom selected from O, S and $NR^5$. Within this subset of compounds, all other variables are as originally defined.

More particularly, one of $R^a$ and $R^b$ represents H and the other represents $C_{1-6}$alkyl. Within this subset of compounds, all other variables are as originally defined.

Even more particularly, one of $R^a$ and $R^b$ represents H and the other represents ethyl. Within this subset of compounds, all other variables are as originally defined.

Another group of compounds that is particular interest relates to compounds of formula I wherein R2 represents H or Halo. Within this subset of compounds, all other variables are as originally defined.

Another group of compounds that is particular interest relates to compounds of formula I wherein:

$R^3$ is selected from the group consisting of H, $C_{1-6}$alkyl, $C_{1-6}$alkylSR$^6$, and $C_{1-6}$alkylNR$^8$R$^9$;

$R^6$ represents $C_{1-6}$alkyl, Aryl, HET or Aryl-$C_{1-6}$alkyl, said alkyl, aryl, and the alkyl group and alkyl portions being optionally substituted with 1–3 members selected from the group consisting of: OH, halo, $NH_2$, $NHCH_3$, $N(CH_3)_2$, $CO_2H$, $CF_3$ and $C_{1-4}$ acyl, and said HET being optionally substituted with 1–2 oxo groups and 1–3 groups selected from halo, $C_{1-4}$alkyl, $C_{1-4}$alkoxy, $CF_3$ and $C_{1-4}$ acyl; and $R^8$ and $R^9$ independently represent H, $C_{1-10}$alkyl, Aryl, HET, $C_{1-6}$alkylN($C_{1-6}$alkyl)$_{0-2}$, Aryl-$C_{1-6}$alkyl , $C_{1-6}$alkyl OH, or $C_{1-6}$alkylC$_{1-6}$alkyl , or $R^8$ and $R^9$ are taken in combination with the nitrogen atom to which they are attached and represent a 3–10 membered ring system containing 1–4 heteroatoms selected from O, S, N and optionally substituted with 1–2 oxo groups, and 1–3 groups selected from $C_{1-6}$alkyl, HET, $CO_2R^c$ and $C(O)N(R^c)_2$, said alkyl and alkyl portions being optionally substituted with 1–3 groups selected from halo, $C_{1-3}$alkyl, hydroxyC$_{1-3}$ alkyl, $C_{1-3}$alkoxy, $C_{1-3}$alkoxyC$_{1-3}$alkyl and Aryl$^1$. Within this subset, all other variables are as originally defined.

More particularly, a group of compounds that is of interest relates to compounds of formula I wherein:

$R^3$ is selected from the group consisting of: H, $C_{1-6}$alkyl, $C_{1-6}$alkylSR$^6$ and $C_{1-6}$alkylNR$^8$R$^9$;

$R^6$ represents Aryl, HET or Aryl-$C_{1-6}$alkyl, said alkyl, aryl, and the alkyl group and alkyl portions being optionally substituted with 1–3 members selected from the group consisting of: OH, halo, $NH_2$, $NHCH_3$, $N(CH_3)_2$, $CO_2H$, $CF_3$ and $C_{1-4}$ acyl, and said HET being optionally substituted with 1–2 oxo groups and 1–3 groups selected from halo and $C_{1-4}$alkyl; and $R^8$ and $R^9$ independently represent H, $C_{1-10}$alkyl, Aryl, HET, $C_{1-6}$alkylN($C_{1-6}$alkyl)$_{0-2}$, Aryl-$C_{1-6}$alkyl or $C_{1-6}$alkylOC$_{1-6}$alkyl , or $R^8$ and $R^9$ are taken combination with the nitrogen atom to which they are attached and represent a 3–10 membered ring system containing 1–4 heteroatoms selected from O, S, N and optionally substituted with 1–2 oxo groups, and 1–3 groups selected from $C_{1-6}$alkyl, HET, $CO_2R^c$ and $C(O)N(R^c)_2$, said alkyl and alkyl portions being optionally substituted with 1–3 groups selected from halo, $C_{1-3}$alkyl, $C_{1-3}$alkoxyC$_{1-3}$alkyl and Aryl$^1$. Within this subset, all other variables are as originally defined.

Another subgroup of compounds that is of particular interest relates to compounds of formula I wherein $R^{10}$ represents H, $C_{1-8}$ alkyl or aryl. Within this subset, all other variables are as previously described.

More particularly, the subgroup of compounds that is of particular interest relates to compounds of formula I wherein $R^{10}$ is selected from the group consisting of: H, methyl, ethyl, isopropyl, t-butyl and phenyl. Within this subset, all other variables are as previously described.

Another subgroup of compounds that is of particular interest relates to compounds of formula I wherein n is 1–6. More particularly, the subgroup of particular interest relates to compounds of formula I wherein n is 1–3. Within this subset, all other variables are as previously described.

One subgroup of compounds that is of particular interest relates to compounds of formula I wherein:

$R^1$ represents HET or Aryl, said HET representing a 5 to 15 membered aromatic, partially aromatic or non-aromatic ring or ring system, containing from 1–4 heteroatoms selected from O, S and N, and optionally substituted with 1–2 groups selected from oxo, halo, $C_{1-4}$alkyl $C_{1-4}$alkoxy and $C_{1-4}$acyl, and said Aryl being selected from phenyl and naphthyl, and being optionally substituted with 1–3 members selected from the group consisting of: OH, Aryl$^1$, HET, halo, $NH_2$, $NHCH_3$, $N(CH_3)_2$, $CO_2H$ and $C_{1-4}$-acyl;

$R^c$ and $R^d$ represent H, and n is an integer of from 0–3 inclusive;

$R^a$ and $R^b$ independently represent H or $C_{1-6}$alkyl optionally substituted with halo, $OR^4$, $SR^4$ or $C_{5-7}$cycloalkyl optionally containing one heteroatom selected from O, S and $NR^5$;

$R^3$ is selected from the group consisting of H, $C_{1-6}$alkyl, $C_{1-6}$alkylSR$^6$, and $C_{1-6}$alkylNR$^8$R$^9$;

$R^6$ represents $C_{1-6}$alkyl, Aryl, HET or Aryl-$C_{1-6}$alkyl, said alkyl, aryl, and the alkyl group and alkyl portions being optionally substituted with 1–3 members selected from the group consisting of: OH, halo, $NH_2$, $NHCH_3$, $N(CH_3)_2$, $CO_2H$, $CF_3$ and $C_{1-4}$ acyl, and said HET being optionally substituted with 1–2 oxo groups and 1–3 groups selected from halo, $C_{1-4}$alkyl, $C_{1-4}$alkoxy, $CF_3$ and $C_{1-4}$ acyl; and $R^8$ and $R^9$ independently represent H, $C_{1-10}$alkyl, Aryl, HET, $C_{1-6}$alkylN($C_{1-6}$alkyl)$_{0-2}$, Aryl-$C_{1-6}$alkyl , $C_{1-6}$alkylOH, or $C_{1-6}$alkylOC$_{1-6}$alkyl , or $R^8$ and $R^9$ are taken in combination with the nitrogen atom to which they are attached and represent a 3–10 membered ring system containing 1–4 heteroatoms selected from O, S, N and optionally substituted with 1–2 oxo groups, and 1–3 groups selected from $C_{1-6}$alkyl, HET, $CO_2R^c$ and $C(O)N(R^c)_2$, said alkyl and alkyl portions being optionally substituted with 1–3 groups selected from halo, $C_{1-3}$alkyl, hydroxyC$_{1-3}$ alkyl, $C_{1-3}$alkoxy, $C_{1-3}$alkoxyC$_{1-3}$alkyl and Aryl$^1$, and $R^{10}$ represents H, $C_{1-8}$ alkyl or aryl. Within this subset, all other variables are as originally defined.

Representative examples of compounds of formula I are found in Table 1 below.

TABLE 1

| Compound Number | Molecular Structure | m/z |
|---|---|---|
| 1 | 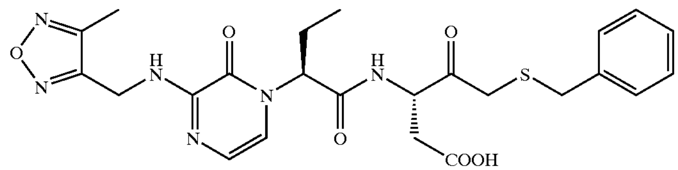 | −ESI: 527.1 (M − 1) |
| 2 | 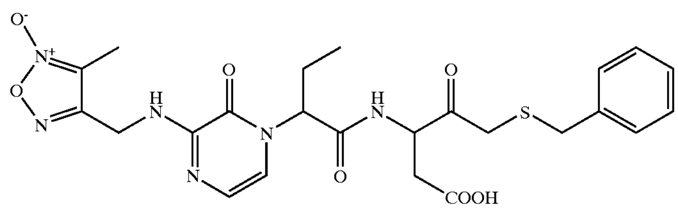 | −ESI: 543.0 (M − 1) |
| 3 | 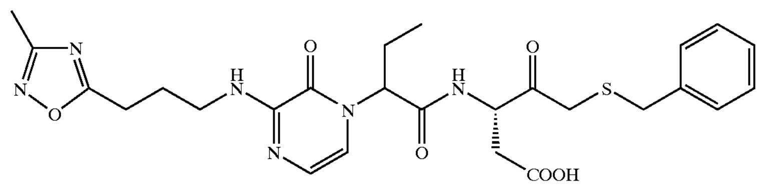 | −APCI: 555.4 (M − 1) |
| 4 | 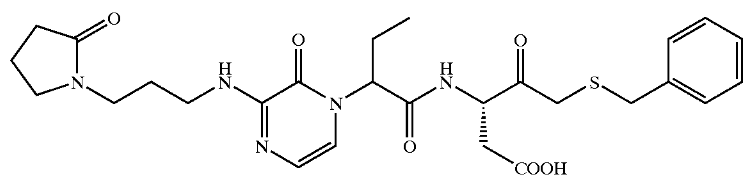 | −APCI: 556.4 (M − 1) |
| 5 | 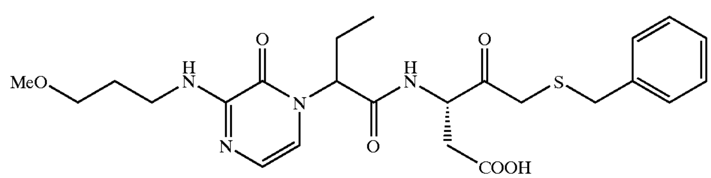 | +APCI: 505.3 (M + 1) |
| 6 | 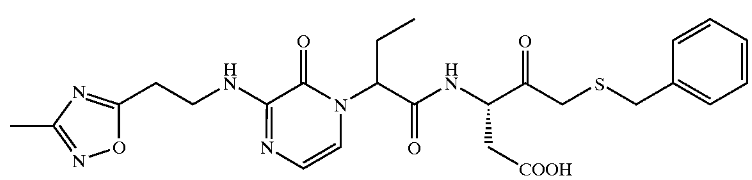 | +ESI: 542.8 (M + 1) |
| 7 | 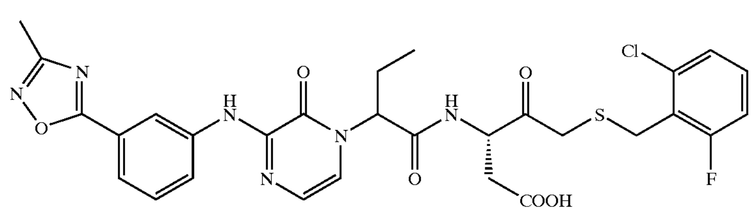 | −ESI: 641.3 (M − 1) |

TABLE 1-continued

| Compound Number | Molecular Structure | m/z |
|---|---|---|
| 8 | 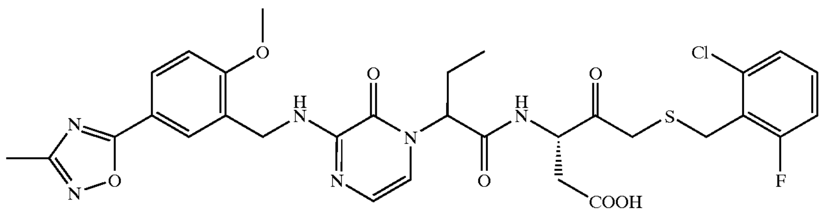 | +ESI: 689.0 (M + 1) |
| 9 | 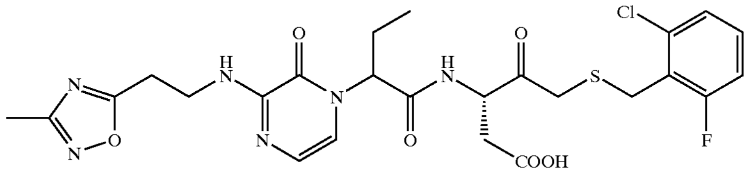 | −ESI: 593.4 (M − 1) |
| 10 | 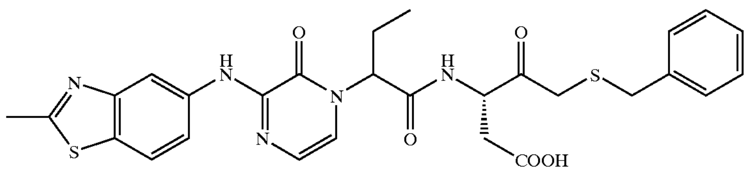 | +APCI: 580.6 (M + 1) |
| 11 | 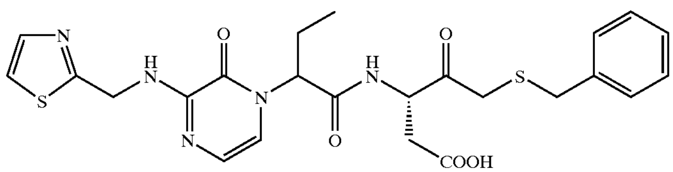 | −APCI: 528.4 (M − 1) |
| 12 | 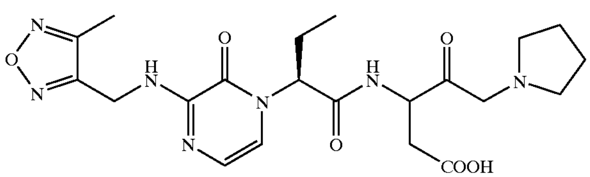 | +ESI: 477.1 (M + 1) |
| 13 | 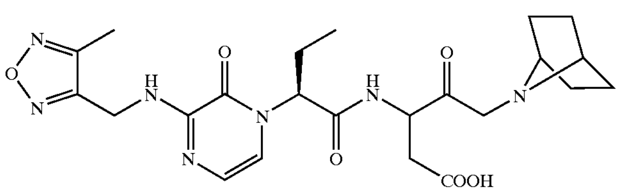 | +ESI: 503.1 (M + 1) |
| 14 | 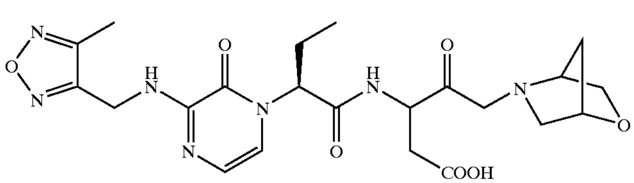 | +ESI: 505.1 (M + 1) |
| 15 | 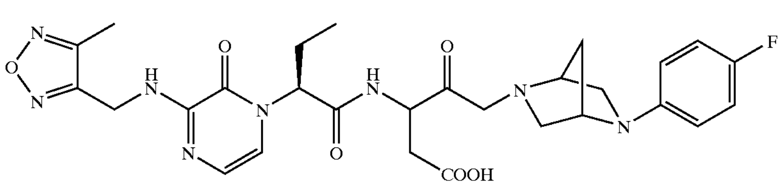 | +ESI: 596.9 (M + 1) |

TABLE 1-continued

| Compound Number | Molecular Structure | m/z |
|---|---|---|
| 16 | 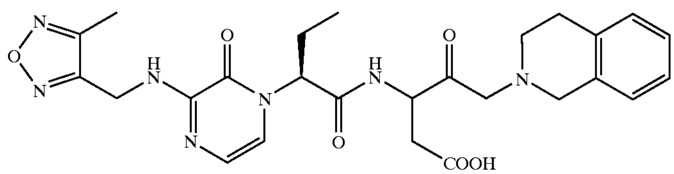 | +ESI: 538.0 (M + 1) |
| 17 | 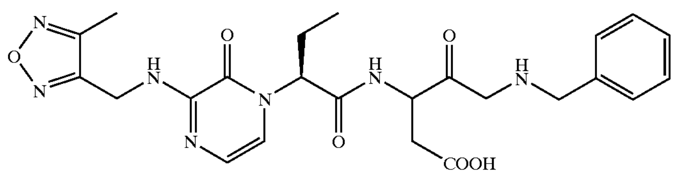 | +ESI: 511.9 (M + 1) |
| 18 | 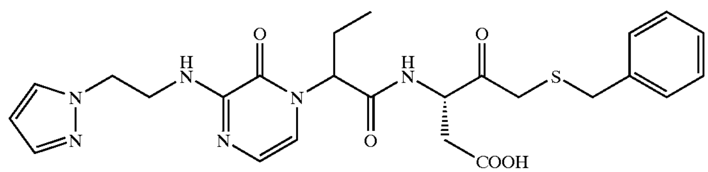 | −APCI: 525.4 (M − 1) |
| 19 | 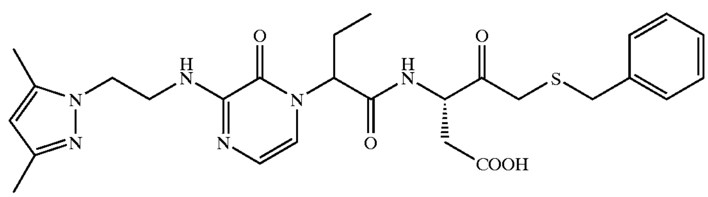 | −APCI: 553.6 (M − 1) |
| 20 | 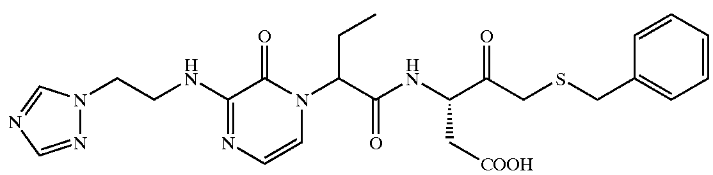 | −ESI: 526.5 (M − 1) |
| 21 | 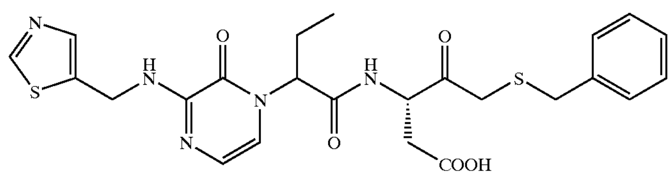 | −ESI: 528.6 (M − 1) |
| 22 | 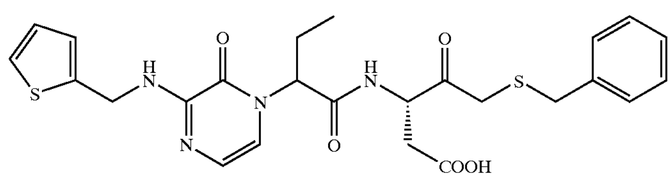 | −ESI: 527.4 (M − 1) |
| 23 | 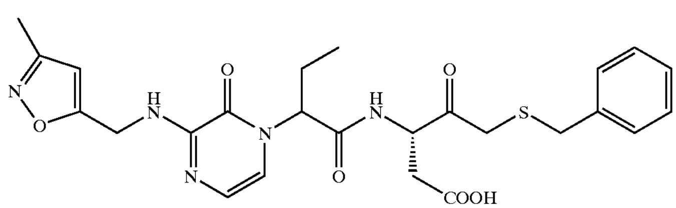 | −ESI: 526.4 (M − 1) |

TABLE 1-continued

| Compound Number | Molecular Structure | m/z |
|---|---|---|
| 24 | 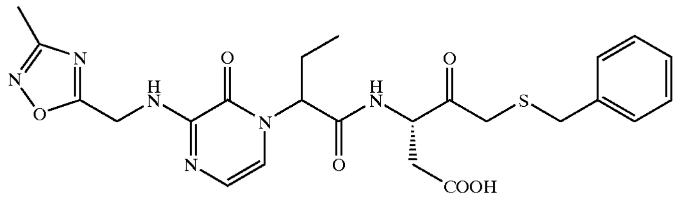 | +ESI: 529.0 (M + 1) |
| 25 | 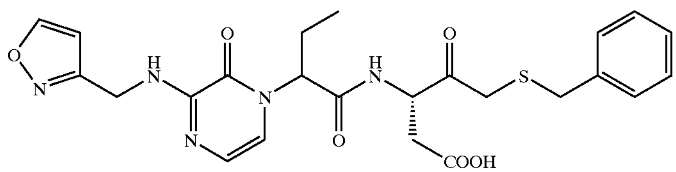 | +ESI: 513.7 (M + 1) |
| 26 | 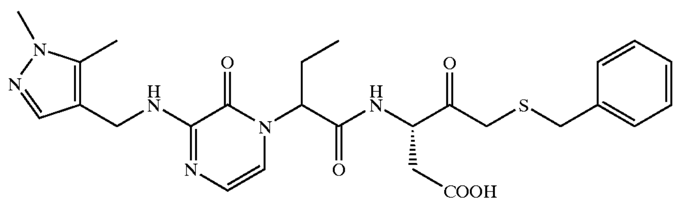 | −ESI: 539.4 (M − 1) |
| 27 | 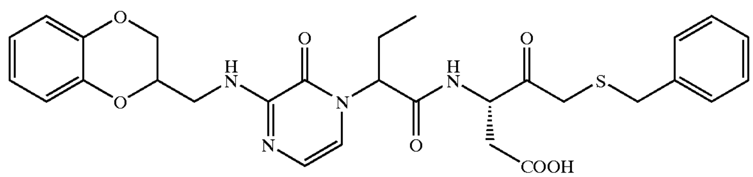 | +ESI: 581.5 (M + 1) |
| 28 | 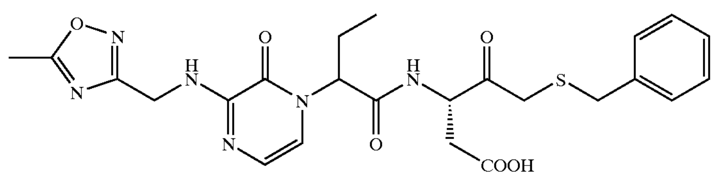 | +ESI: 529.0 (M + 1) |
| 29 | 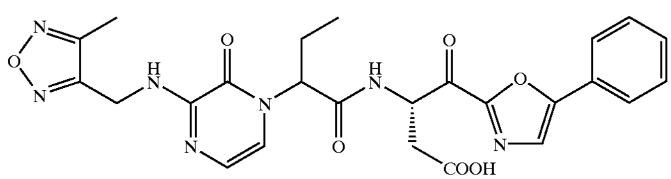 | +APCI: 536.3 (M + 1) |
| 30 | 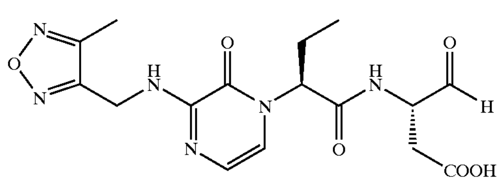 | −ESI: 391.5 (M − 1) |
| 31 | 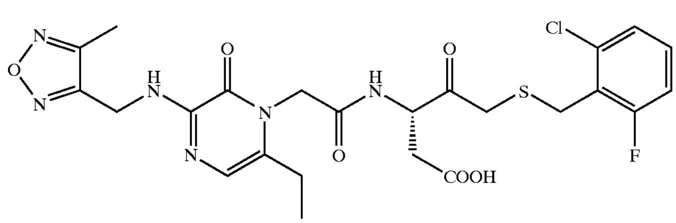 | +APCI: 609.4 (M + 1) |

TABLE 1-continued

| Compound Number | Molecular Structure | m/z |
|---|---|---|
| 32 | 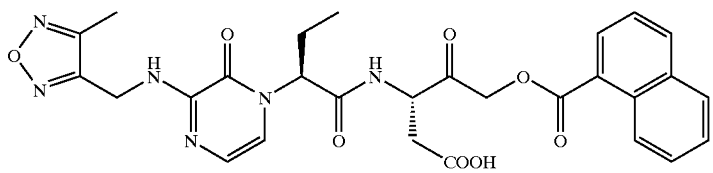 | +ESI: 576.9 (M + 1) |
| 33 | 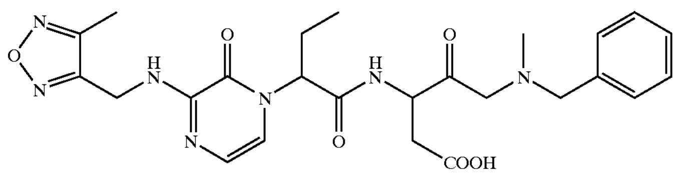 | |
| 34 | 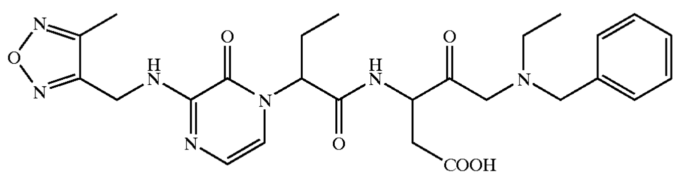 | |
| 35 | 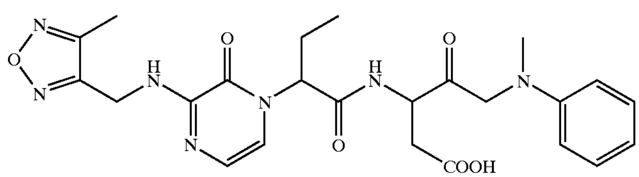 | |
| 36 | 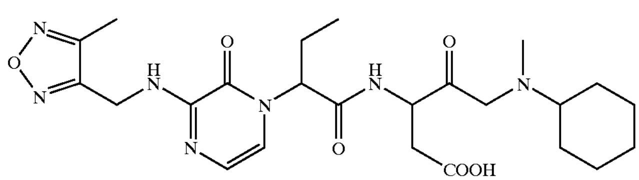 | |
| 37 | 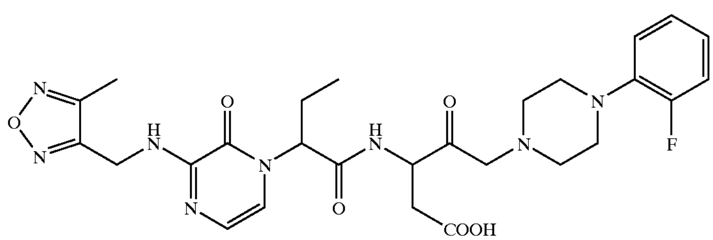 | |
| 38 | 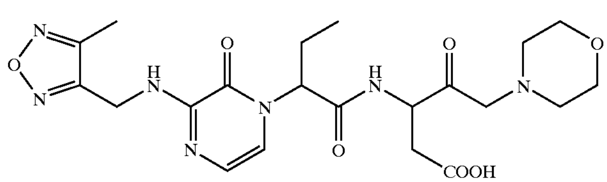 | |
| 39 | 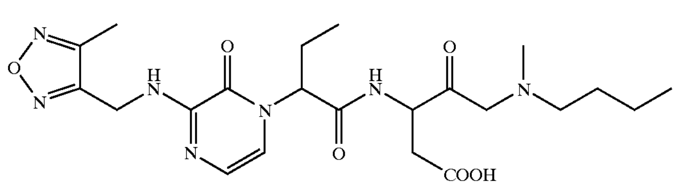 | +ESI: 492.0 (M + 1) |

TABLE 1-continued

| Compound Number | Molecular Structure | m/z |
|---|---|---|
| 40 | 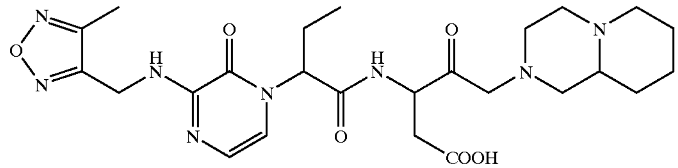 | +ESI: 545.2 (M + 1) |
| 41 | 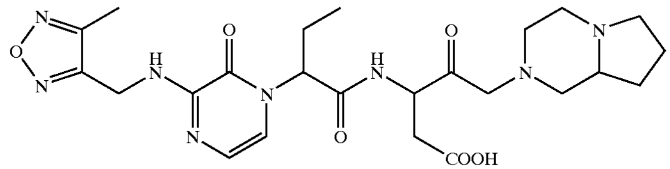 | |
| 42 | 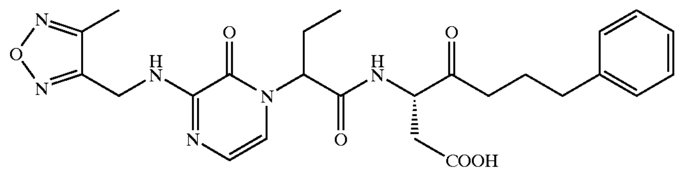 | |
| 43 | 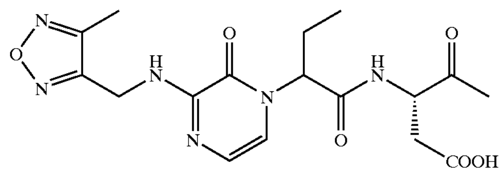 | |
| 44 | 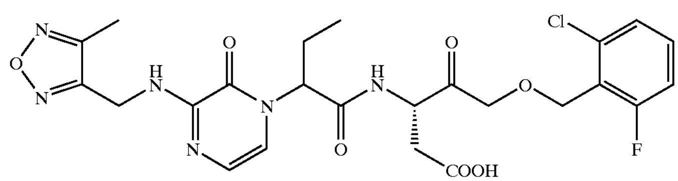 | |
| 45 | 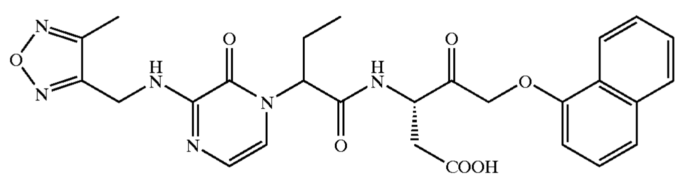 | |
| 46 | 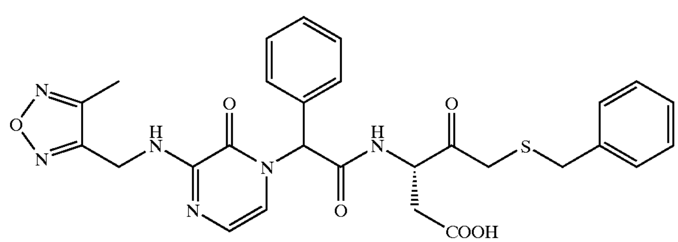 | |
| 47 | 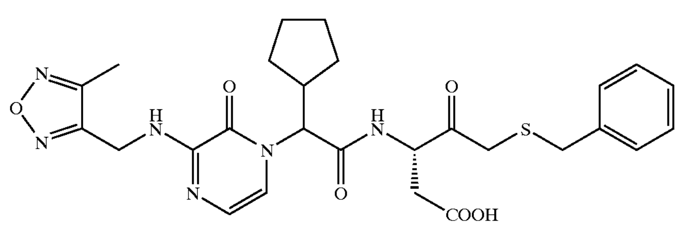 | |

TABLE 1-continued

| Compound Number | Molecular Structure | m/z |
|---|---|---|
| 48 | 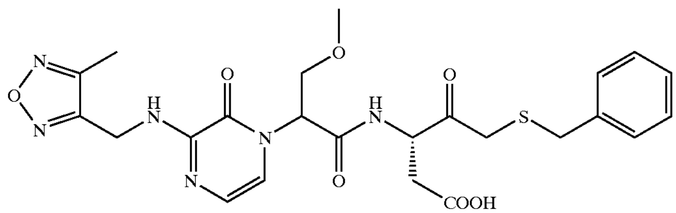 | |
| 49 | 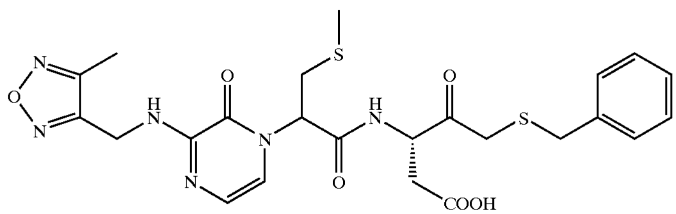 | |
| 50 | 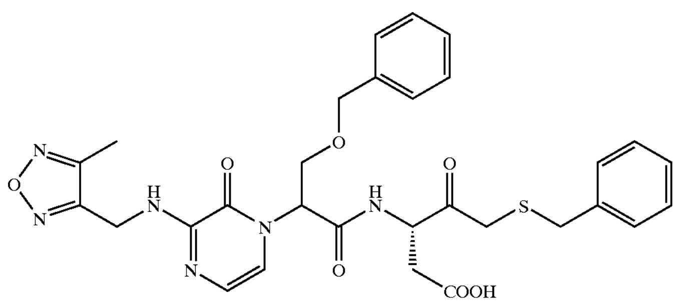 | |
| 51 | 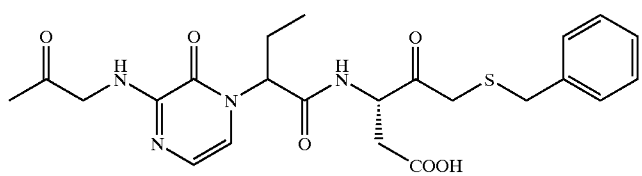 | |
| 52 | 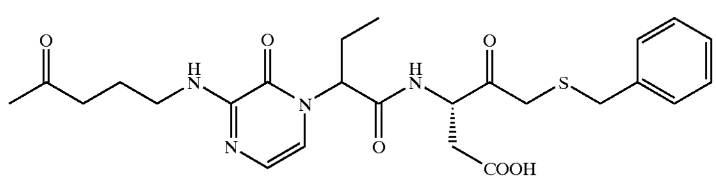 | |
| 53 | 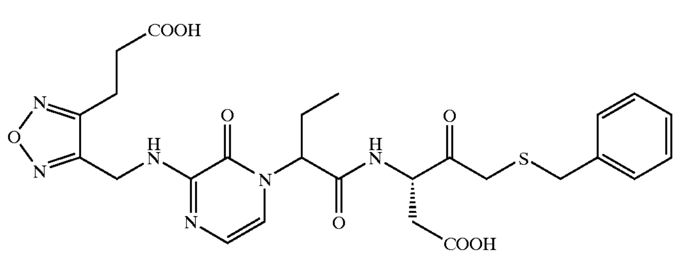 | −APCI: 585.8 (M − 1) |

TABLE 1-continued

| Compound Number | Molecular Structure | m/z |
|---|---|---|
| 54 | 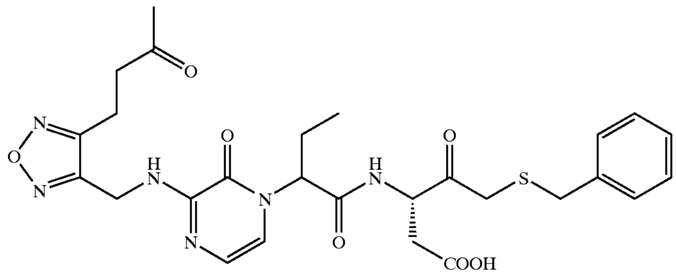 | |
| 55 | 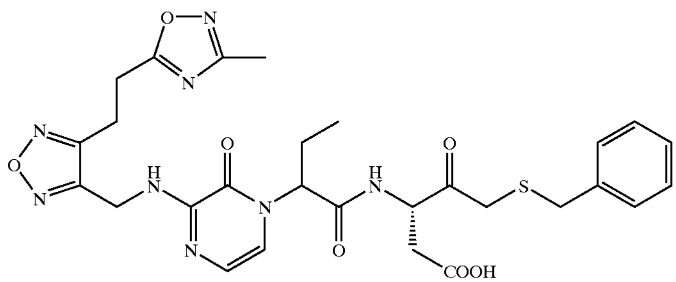 | −APCI: 623.9 (M − 1) |
| 56 | 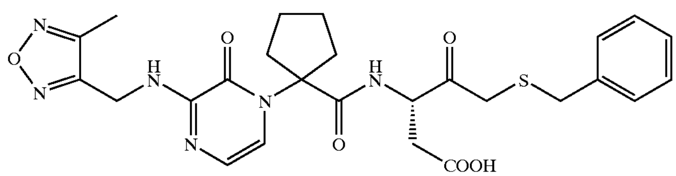 | |
| 57 | 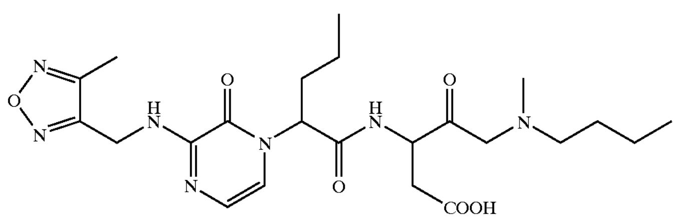 | +APCI: 543.3 (M + 1) |
| 58 | 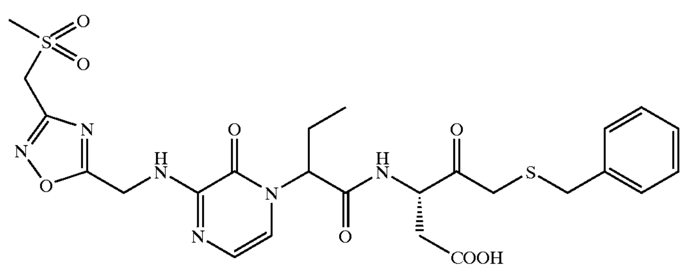 | |
| 59 | 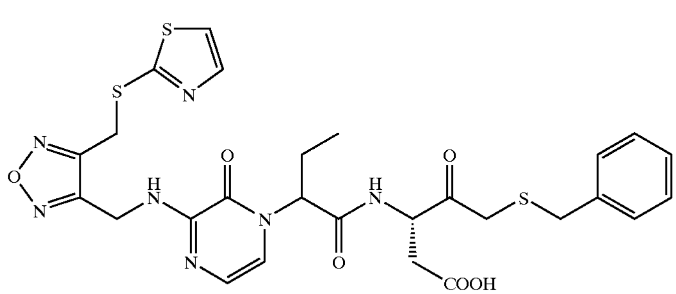 | +APCI: 644.3 (M + 1) |

TABLE 1-continued

| Compound Number | Molecular Structure | m/z |
|---|---|---|
| 60 | 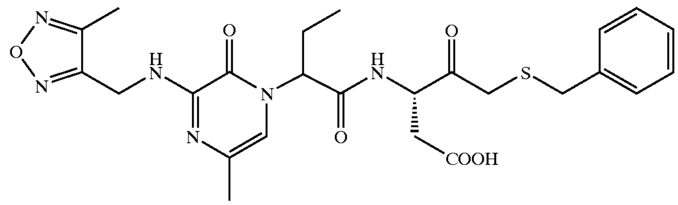 | −APCI: 541.7 (M − 1) |
| 61 | 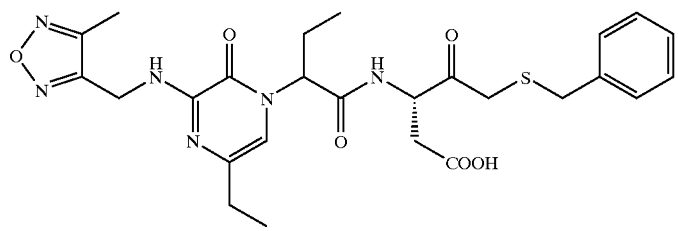 | −APCI: 555.5 (M − 1) |
| 62 | 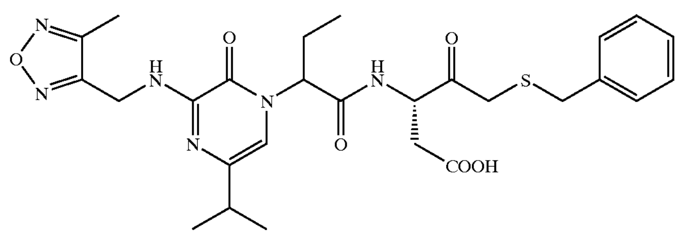 | −APCI: 569.4 (M − 1) |
| 63 | 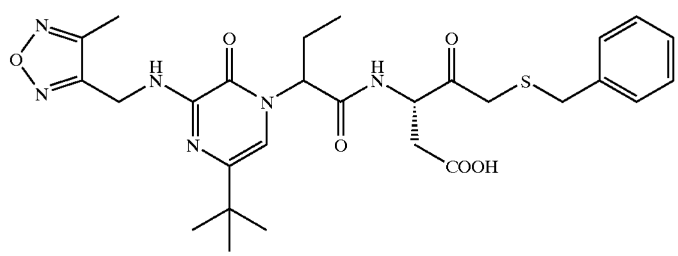 | +ESI: 607.4 (M + Na⁺) |
| 64 | 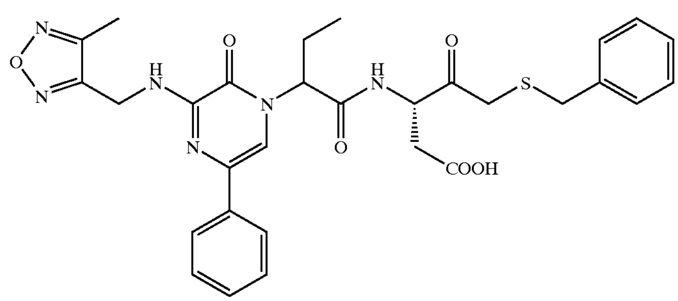 | −APCI: 603.1 (M − 1) |
| 65 | 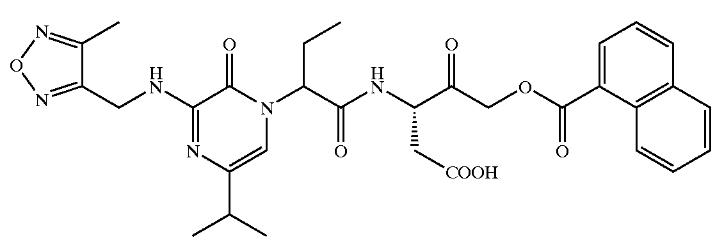 | |

TABLE 1-continued

| Compound Number | Molecular Structure | m/z |
|---|---|---|
| 66 | 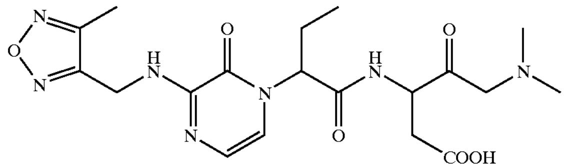 | +ESI: 450.1 (M + 1) |
| 67 | 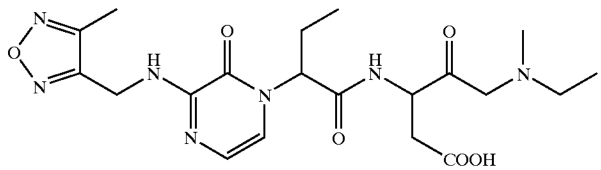 | +ESI: 464.0 (M + 1) |
| 68 | 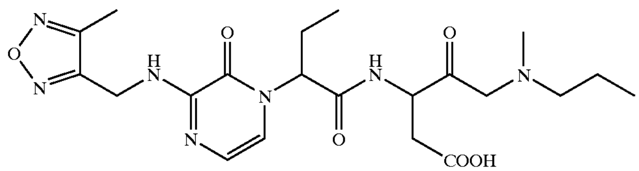 | +ESI: 478.1 (M + 1) |
| 69 | 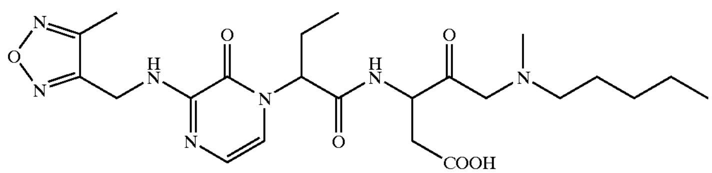 | +ESI: 506.2 (M + 1) |
| 70 | 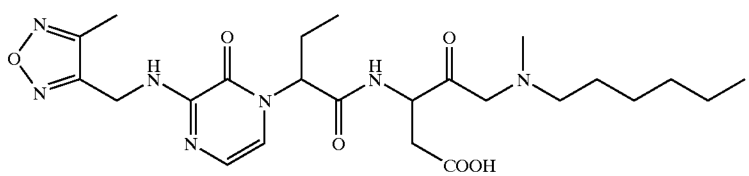 | +ESI: 519.9 (M + 1) |
| 71 | 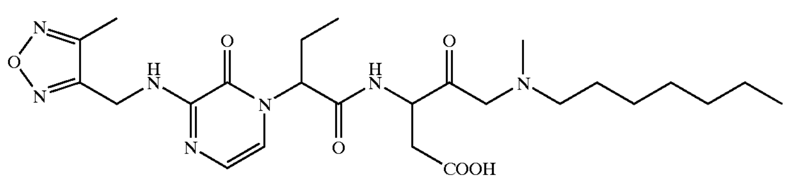 | +ESI: 546.5 (M + 1) |
| 72 | 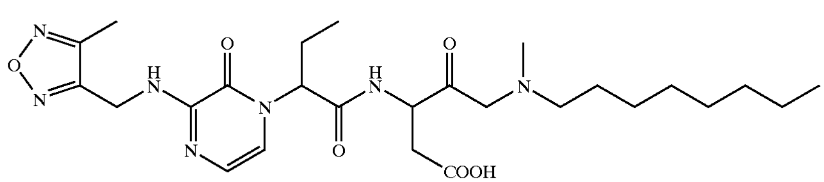 | +ESI: 546.5 (M + 1) |
| 73 | 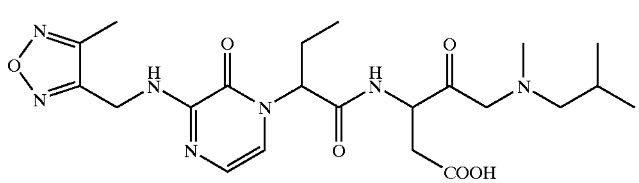 | −APCI: 490.5 (M − 1) |

TABLE 1-continued

| Compound Number | Molecular Structure | m/z |
|---|---|---|
| 75 | 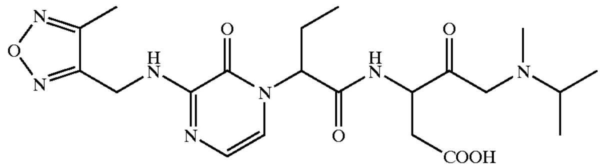 | +ESI: 478.0 (M + 1) |
| 76 | 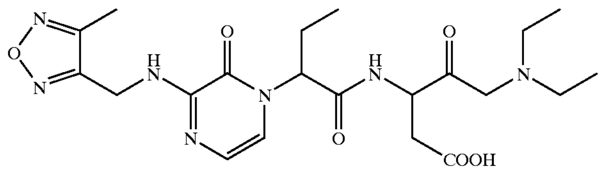 | +ESI: 478.6 (M + 1) |
| 77 | 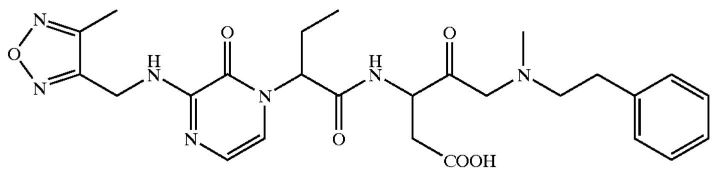 | −APCI: 538.4 (M − 1) |
| 78 | 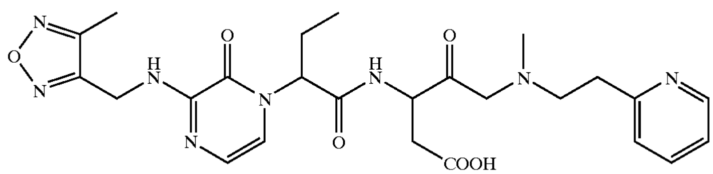 | +ESI: 540.9 (M + 1) |
| 79 | 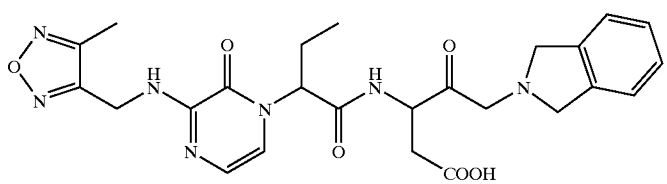 | +ESI: 524.0 (M + 1) |
| 80 | 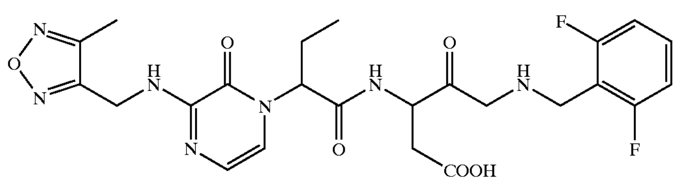 | −APCI: 546.6 (M − 1) |
| 81 | 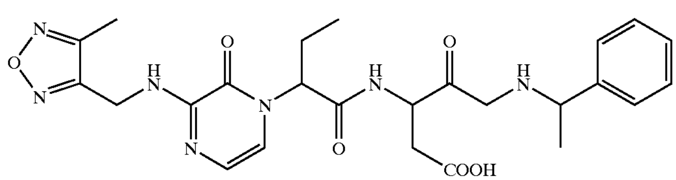 | +ESI: 526.0 (M + 1) |
| 82 | 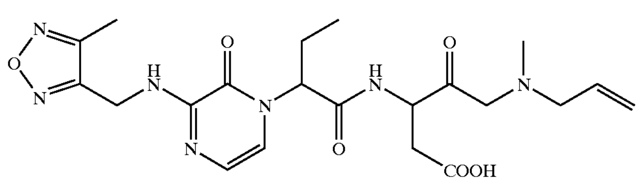 | +ESI: 474.5 (M + 1) |

TABLE 1-continued

| Compound Number | Molecular Structure | m/z |
|---|---|---|
| 83 | 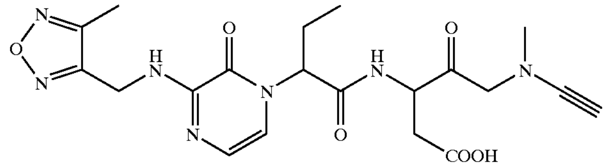 | +ESI: 474.6 (M + 1) |
| 84 | 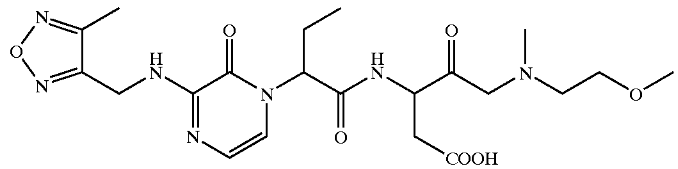 | +ESI: 492.7 (M + 1) |
| 85 | 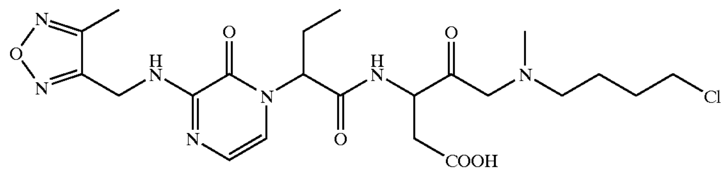 | |
| 86 | 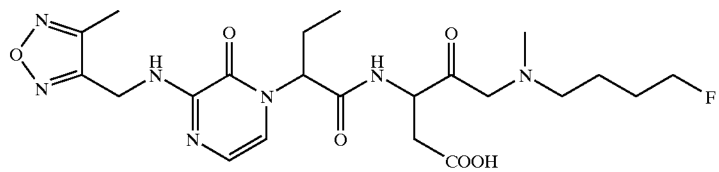 | |
| 87 | 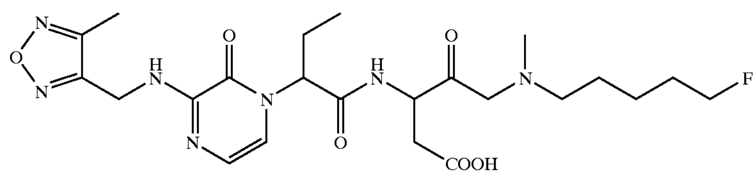 | |
| 88 | 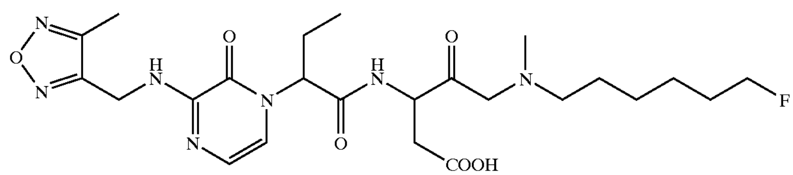 | +ESI: 536.3 (M + 1) |
| 89 | 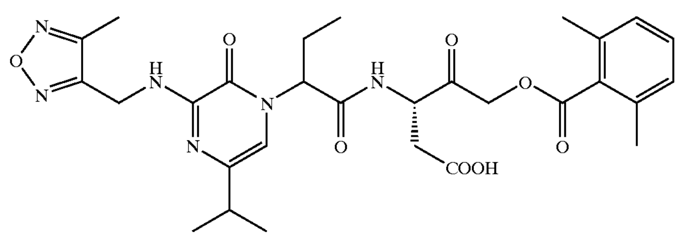 | |
| 90 | 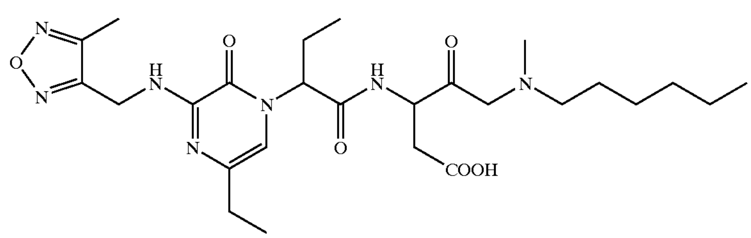 | +ESI: 548.3 (M + 1) |

TABLE 1-continued

| Compound Number | Molecular Structure | m/z |
|---|---|---|
| 91 | 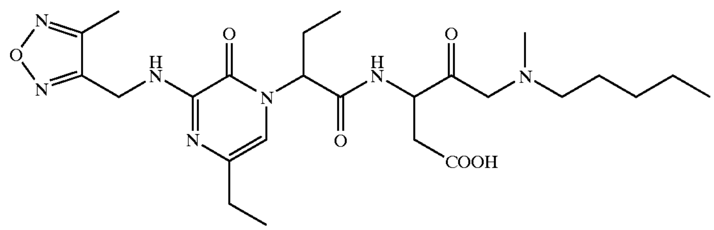 | +ESI: 534.3 (M + 1) |
| 92 | 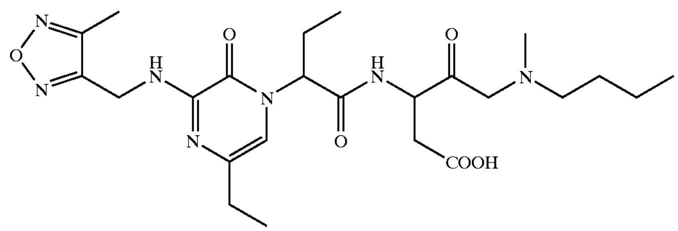 | +ESI: 520.4 (M + 1) |
| 93 | 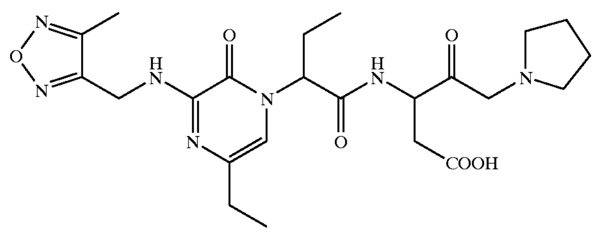 | +APCI: 504.6 (M + 1) |
| 94 | 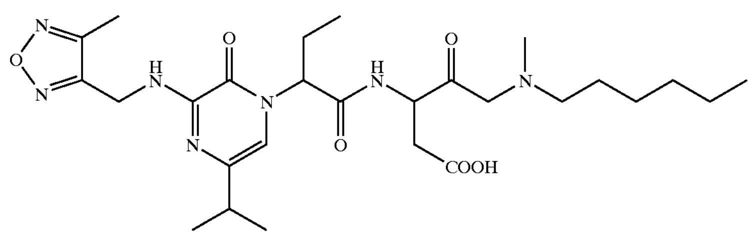 | +APCI: 562.5 (M + 1) |
| 95 | 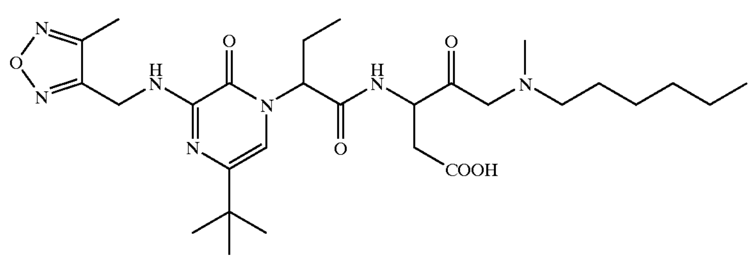 | +APCI: 576.5 (M + 1) |
| 96 | 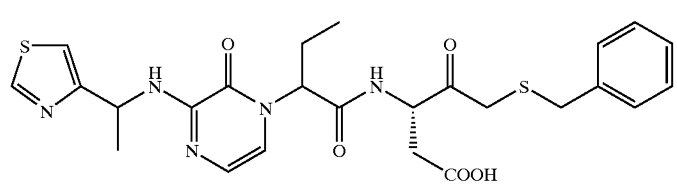 | +ESI: 542.9 (M + 1) |

TABLE 1-continued

| Compound Number | Molecular Structure | m/z |
|---|---|---|
| 97 | 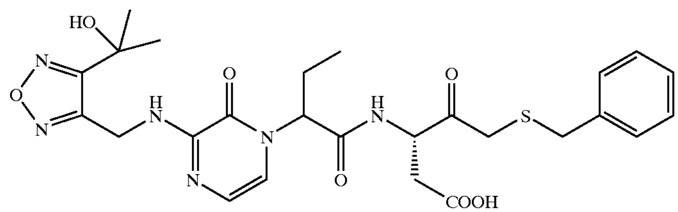 | −APCI: 571.3 (M − 1) |
| 98 | 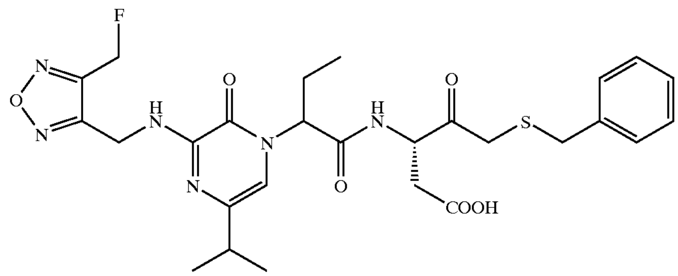 | |
| 99 | 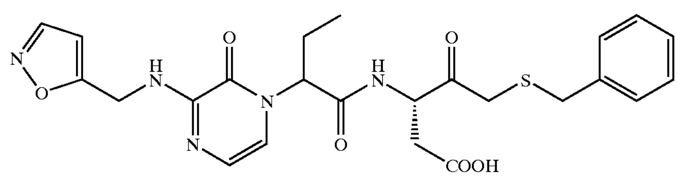 | −APCI: 512.4 (M − 1) |
| 100 | 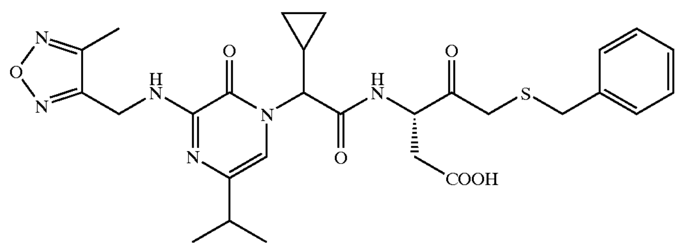 | |
| 101 | 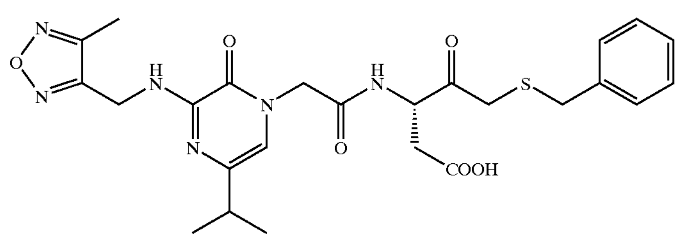 | +APCI: 543.1 (M + 1) |
| 102 | 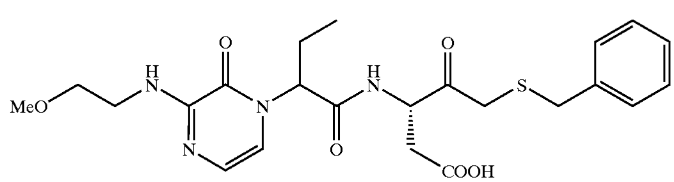 | +ESI: 490.9 (M + 1) |
| 103 | 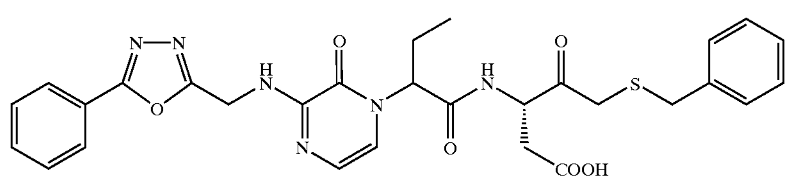 | −APCI: 589.3 (M − 1) |

TABLE 1-continued

| Compound Number | Molecular Structure | m/z |
|---|---|---|
| 104 | (structure) | +APCI: 506.3 (M + 1) |
| 105 | (structure) | |

The compounds described herein, and in particular, in Table 1, are intended to include salts, enantiomers, esters, N-oxides and hydrates, in pure form and as a mixture thereof. While chiral structures are shown below, by substituting into the synthesis schemes an enantiomer other than the one shown, or by substituting into the schemes a mixture of enantiomers, a different isomer or a racemic mixture can be achieved. Thus, all such isomers and mixtures are included in the present invention.

In another embodiment, the invention encompasses a method of treating or preventing a caspase-3 mediated disease or condition in a mammalian patient in need thereof, comprising administering to said patient a compound of formula I in an amount effective to treat or prevent said caspase-3 mediated disease or condition.

In another embodiment, the invention encompasses a method of treating cardiac and cerebral ischemia/reperfusion injury (e.g. stroke), type I diabetes, immune deficiency syndrome (including AIDS), cerebral and spinal cord trauma injury, organ damage during transplantation, sepsis, bacterial meningitis, alopecia, aging, Parkinson's disease, Alzheimer's disease, Down's syndrome, spinal muscular atrophy, multiple sclerosis and neurodegenerative disorders, comprising administering to a mammalian patient in need of such treatment an effective amount of a compound of formula I.

In another embodiment, the invention encompasses a method of treating acute disorders, including cardiac and cerebral ischemia/reperfusion injury (e.g. stroke), sepsis, bacterial meningitis, spinal cord injury and organ damage during transplantation, in a mammalian patient in need of such treatment, comprising administering to said patient a compound of formula I in an amount effective to treat said acute disorder.

In another embodiment, the invention encompasses a method of treating chronic disorders, including neurodegenerative diseases (e.g. Alzheimer's, polyglutamine-repeat disorders, Down's, spinal muscular atrophy, multiple sclerosis), immunodeficiency (e.g. HIV), diabetes, alopecia and aging, in a mammalian patient in need of such treatment, comprising administering to said patient a compound of formula I in an amount effective to treat said chronic disorder.

In another embodiment, the invention encompasses a method of treating a caspase-3 mediated disease in a mammalian patient in need of such treatment, comprising administering to said patient a compound of formula I in an amount effective to treat said caspase-3 mediated disease.

In particular, these compounds are preferably useful to treat, prevent or ameliorate in mammals and especially in humans, diseases including but not limited to:

cardiac and cerebral ischemia/reperfusion injury (e.g. stroke)
type I diabetes
immune deficiency syndrome (including AIDS)
cerebral and spinal cord trauma injury
organ damage during transplantation
alopecia
aging
sepsis
bacterial meningitis
Parkinson's disease
Alzheimer's disease
Down's syndrome
spinal muscular atrophy
multiple sclerosis
neurodegenerative disorders.

The compound is adminstered to a mammalian patient in need of such treatment or prevention an amount of a compound as described herein that is effective to treat or prevent the disease or condition.

The compounds described typically contain asymmetric centers and may thus give rise to diastereomers and optical isomers. The present invention is meant to comprehend such possible diastereomers as well as their racemic and resolved, enantiomerically pure forms and pharmaceutically acceptable salts thereof.

The pharmaceutical compositions of the present invention comprise a compound of formula I as an active ingredient or a pharmaceutically acceptable salt thereof in combination with a pharmaceutically acceptable carrier, and optionally other therapeutic ingredients. The term "pharmaceutically acceptable salts" refers to salts prepared from pharmaceutically acceptable bases including inorganic bases and organic bases. Representative salts derived from inorganic bases include aluminum, ammonium, calcium, copper, ferric, ferrous, lithium, magnesium, manganic salts, manganous, ammonium, potassium, sodium, zinc and the like. Particularly preferred are the calcium, magnesium, potassium, and sodium salts. Representative salts derived from pharmaceutically acceptable organic bases include salts of primary, secondary and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, salts may be prepared from pharmaceutically acceptable non-toxic acids, including inorganic and organic acids. Examples of such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric and tartaric acids.

In the discussion of methods of treatment which follows, reference to the compounds of formula I are meant to also include the pharmaceutically acceptable salts.

The ability of the compounds of formula I to inhibit caspase-3 make them useful research tools in the field of apoptosis.

The magnitude of therapeutic dose of a compound of formula I will, of course, vary with the nature of the severity of the condition to be treated and with the particular compound of formula I and its route of administration and vary upon the clinician's judgement. It will also vary according to the age, weight and response of the individual patient. An effective dosage amount of the active component can thus be determined by the clinician after a consideration of all the criteria and using is best judgement on the patient's behalf. A representative dose will range from 0.001 mpk/d to about 100 mpk/d.

An ophthalmic preparations for ocular administration comprising 0.001–1% by weight solutions or suspensions of the compounds of formula I in an acceptable ophthalmic formulation may be used.

Any suitable route of administration may be employed for providing an effective dosage of a compound of the present invention. For example, oral, parenteral and topical may be employed. Dosage forms include tablets, troches, dispersions, suspensions, solutions, capsules, creams, ointments, aerosols, and the like.

The compositions include compositions suitable for oral, parenteral and ocular (ophthalmic). They may be conveniently presented in unit dosage form and prepared by any of the methods well-known in the art of pharmacy.

In practical use, the compounds of formula I can be combined as the active ingredient in intimate admixture with a pharmaceutical carrier according to conventional pharmaceutical compounding techniques. The carrier may take a wide variety of forms depending on the form of preparation desired for administration. In preparing the compositions for oral dosage form, any of the usual pharmaceutical media may be employed, such as, for example, water, alcohols, oils, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case or oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

Pharmaceutical compositions of the present invention suitable for oral administration may be presented as discrete units such as capsules, cachets or tablets each containing a predetermined amound of the active ingredient, as a powder or granules or as a solution or a suspension in an aqueous liquid, a non-aqueous liquid, an oil-in-water emulsion or a water-in-oil emulsion. Such compositions may be prepared by any of the methods of pharmacy but all methods include the step of bringing into active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. For example, each dosage unit may contain from about 0.01 mg to about 1.0 g of the active ingredient.

Method of Synthesis

Compounds of the present invention are conveniently prepared using the procedures described generally below and more explicitly described in the Example section thereafter.

Scheme 1: Preparation of Bromomethyl Ketone 1

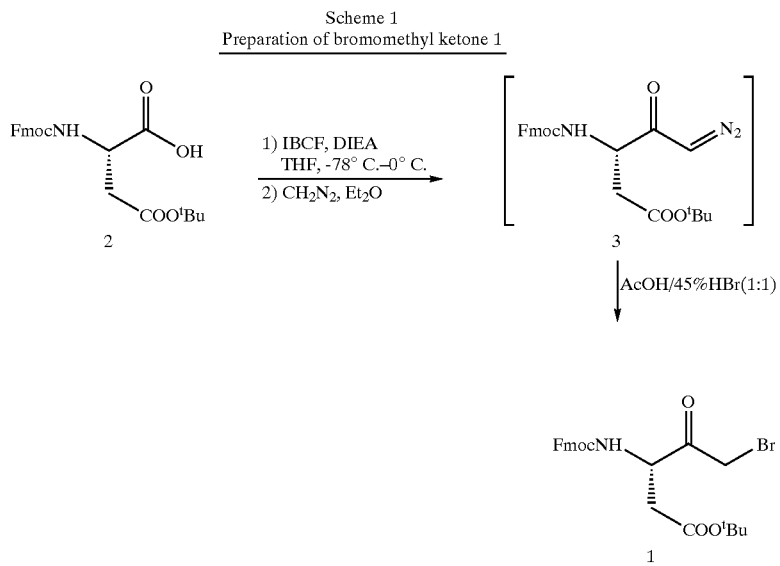

Bromomethyl ketone 1 is prepared as illustrated in Scheme 1. Reaction of N-fluorenylmethyloxycarbonyl-L-aspartic acid β-tert-butyl ester (Fmoc-L-Asp (OtBu)-OH) (2) (Novabiochem) with iso-butyl chloroformate (IBCF) followed by treating the reaction mixture with an excess of diazomethane yields the diazomethylketone intermediate 3. This intermediate is subjected in situ to a 1:1 mixture of AcOH and 45% aqueous hydrobromic acid (HBr) to give compound 2 as a white powder.

The semicarbazide resin A is prepared according to Scheme 2. Treatment of compound 4 (Webb et al, J. Am. Chem. Soc. 114, 3156 (1992)) with a commercial amino-Merrifield resin in the presence of EDCI and HOBT in dichloromethane followed by removal of the Boc group with trifluoroacetic acid (TFA) in dichloromethane afforded resin A.

Scheme 2: Preparation of Semicarbazide Resin A

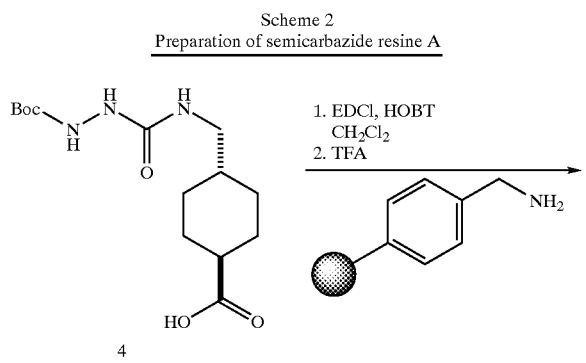

-continued

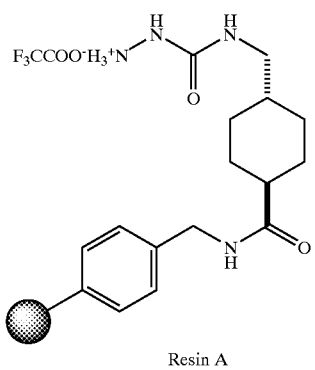

The general procedure for the solid phase synthesis of compound of general structure Ia incorporating a sulfide P1' side chain, a P1' carboxylate side chain and a phenoxide side chain is illustrated in Scheme 3.

Bromomethyl ketone 1 is mixed with resin A in THF in the presence of AcOH overnight to furnish resin B. Nucleophilic displacement with an appropriate nucleophile in the presence of suitable bases followed by deprotection of the Fmoc protecting group using piperidine in DNE to give resin C as shown. Resin C is first reacted with pyrazinone acids of general structure II using O-(7-Azabenzotriazol-1-yl)N,N,N',N'-tetramethyluronium hexafluorophosphate as the activating agent and DIEA as the base, and the resultant resin is treated with a cocktail of TFA and water (9/1, v/v) to furnish the final Product Ia in which $RXCH_2$ represents $R^3$.

Scheme 3: General Scheme for Preparing Compounds of Structure Type Ia
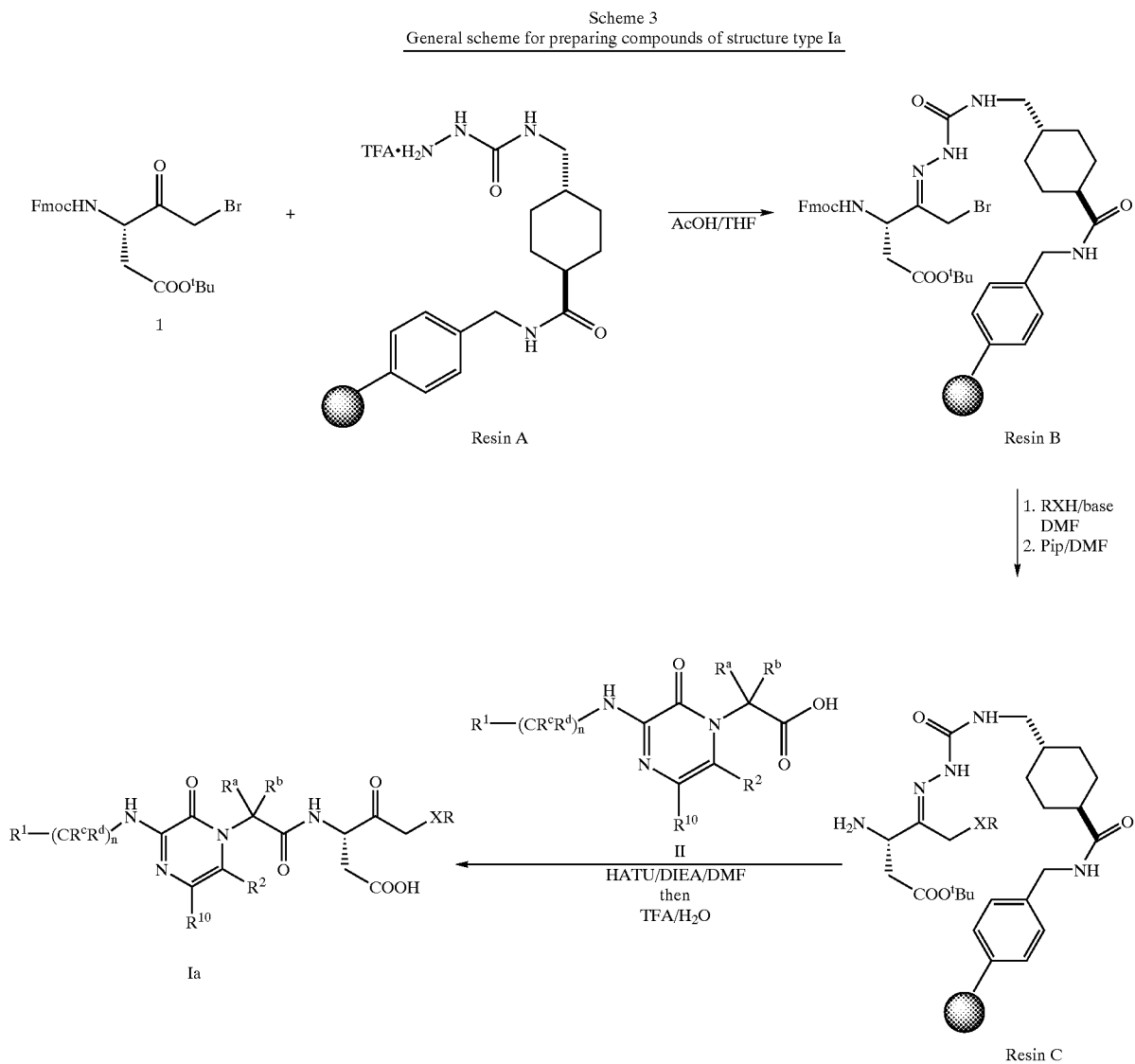

The general scheme for solution phase synthesis of pyrazinone derivatives Ib containing a P1' amino, a P1' carboxylate, a P1' sulfide or a P1' phenoxide is illustrated in Scheme 4.

Scheme 4: General Solution Protocol for Preparation of Compound of Structure Ib

45%HBr/AcOH to yield the bromomethyl ketone 7. 7 is processed to the final product Ib, wherein R'XCH$_2$ represents R$^3$, by first reacting with a suitable nucleophile in the presence of appropriate bases and then with a solution of TFA in dichloromethane.

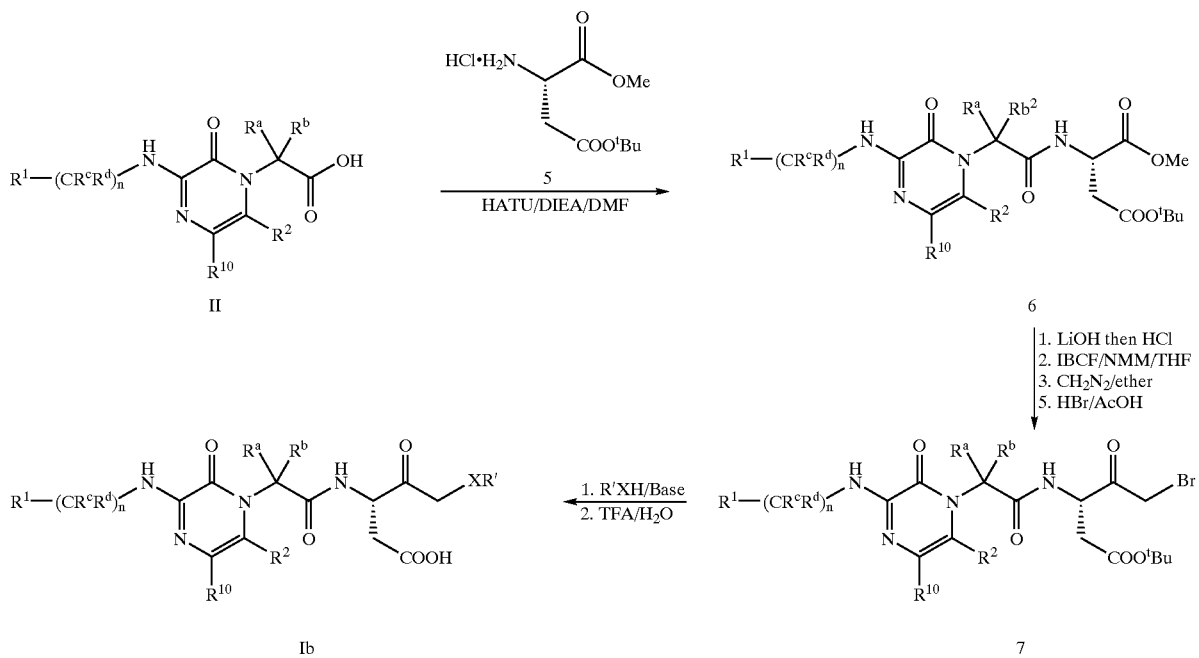

Appropriate pyrazinone acid II is first reacted with β-$^t$butyl aspartic acid methyl ester hydrochloride (5) in the presence of HATU/DIEA in DMF to give structure 6. 6 is then carefully hydrolyzed with LiOH in THF/H$_2$O and acidified. The resultant acid is treated with IBCF in the presence of NMM in THF and the mixed anhydride is reacted in situ with diazomethane in ether/THF. The diazo intermediate is directly treated with a mixture of 1:1 (v/v)

Alternatively as shown in Scheme 5, 6 is carefully hydrolyzed with LiOH in THF/H$_2$O and acidified. The resultant acid is treated with IBCF in the presence of NMM in THF and the mixed anhydride is reduced with NaBH$_4$ to give the corresponding alcohol which is oxidized under the Dess-Martin oxidation conditions to afford aldehydes of general structure Ic. Reaction of Ic with an appropriate oganometallic reagent R"M followed by oxidation affords ketones of general structure Id wherein R" represents R$^3$.

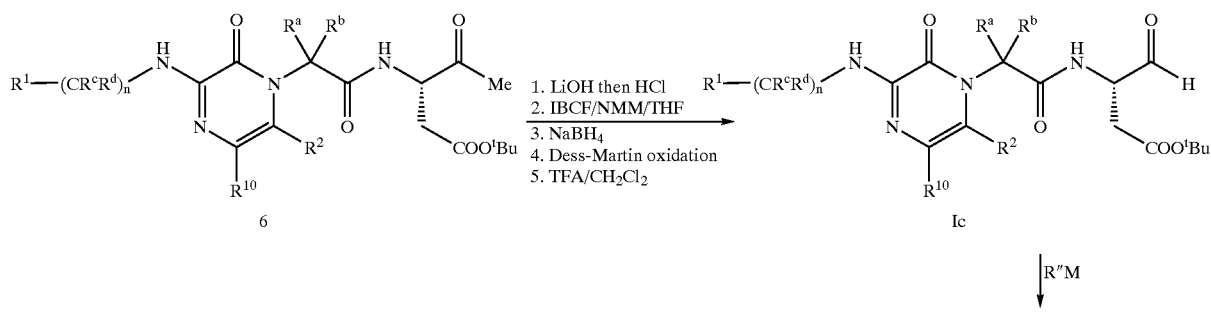

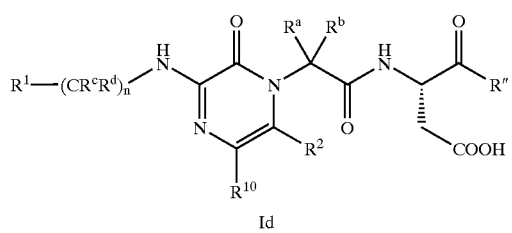
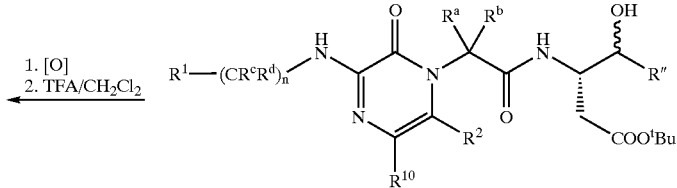

A general protocol for making the pyrazinone core structure II is illustrated in Scheme 6.

SCHEME 6

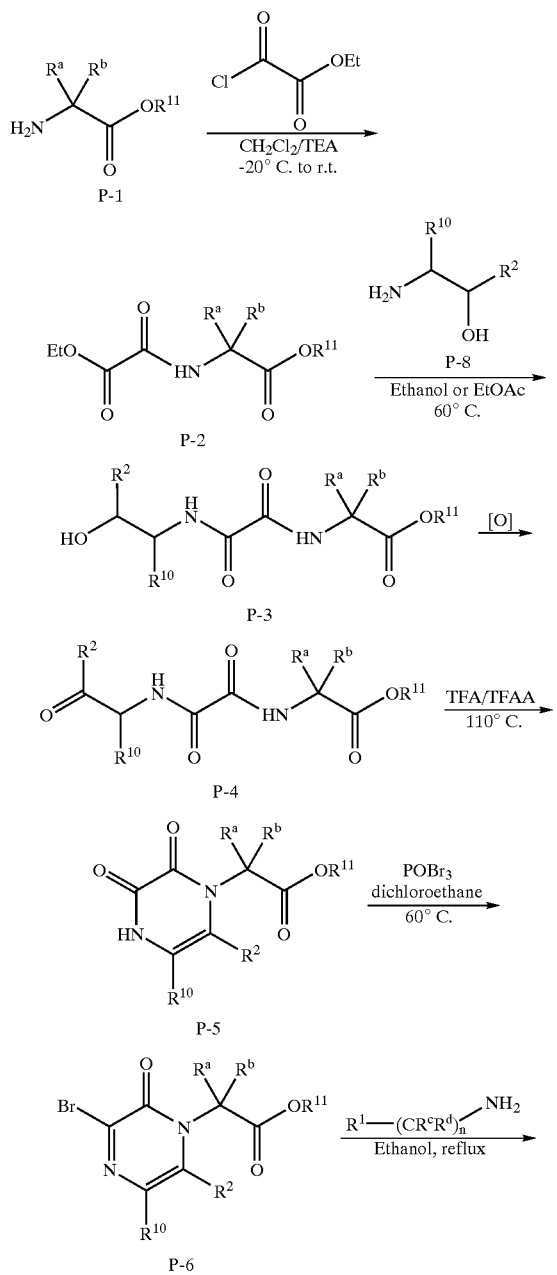
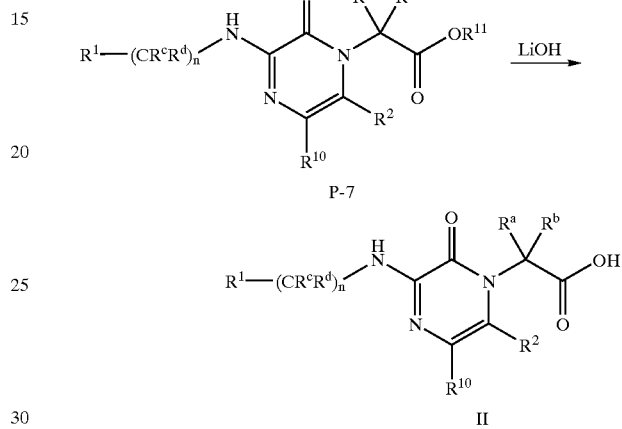

An appropriate amino ester P-1 wherein $R^{11}$ is benzyl, methyl, ethyl, propyl, isopropyl or another suitable protecting group is first reacted with ethyl oxalyl chloride in dichloromethane in the presence of triethylamine to give product P-2. The reaction of P-2 with a suitable amino alcohol P-8 ($R^2$ is hydrogen or alkyl) affords alcohol P-3, which is oxidized to the corresponding ketone P-4. Treatment of P-4 with trifluoroacetic acid (TFA) and trifluoroacetic anhydride (TFAA) in acetic acid at approximately 110° C. furnishes the cyclized product P-5, which is reacted with phosphorus oxybromide (POBr$_3$) to yield the corresponding bromide P-6.

Reaction of bromide P-6 with an appropriate amine $R^1$-(CR$^c$R$^d$)$_n$—NH$_2$ in ethanol at reflux temperature gives ester P-7 which is hydrolyzed to afford the desired acid II. When n is 0, the reaction may require the presence of a base, such as a hydride base.

PREPARATIVE EXAMPLE 1

2-(3-Methyl-1,2,4-oxadiazol-5-yl)-1-ethylamine (23)

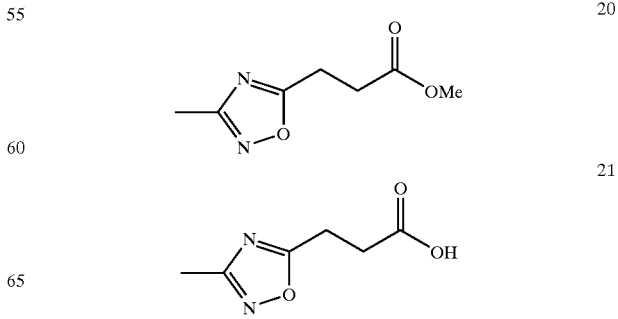

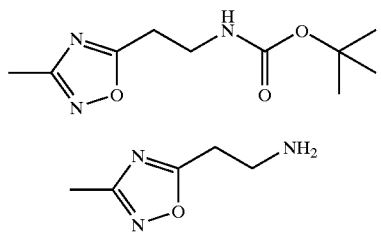

Step 1. A mixture of succinic acid mono-methyl ester (5.28 g), DMAP (4.88 g), methylamidoxime (1.1 eq) and EDCI (1.2 eq) in DME was heated to 95–100° C. for three days and cooled to room temperature. The mixture was then partitioned between ethyl acetate and 1N HCl and the organic phase was washed with brine, dried, filtered and concentrated. The residue was purified by chromatography to afford compound 20 (4.2 g) as a colorless oil. $^1$H NMR (400 MHz, acetone-$d_6$): δ3.62 (s, 3H), 3.13 (t, 2H), 2.86 (t, 2H), 2.27 (s, 3H).

The methyl ester in 20 was hydrolyzed as follow: to a solution of 20 (4.2 g) in ethanol (100 mL) and water (35 mL) was added LiOH monohydrate (2.3 g) and the mixture was stirred for 2 hours and then acidified with 1N HCl. The whole mixture was concentrated in vacuo to approximately 15 mL and then extracted with ethyl acetate (3×). The extracts were combined, washed with brine, dried, filtered and concentrated. The residue was precipitated from ether/hexanes to yield acid 21 (3.6 g) as a white powder. $^1$H NMR (400 MHz, acetone-$d_6$): δ3.12 (t, 2H), 2.88 (t, 2H), 2.27 (s, 3H).

To a solution of acid 21 (500 mg) in t-butyl alcohol was added diphenyl phosphorus azide (0.76 mL) and triethylamine (0.94 mL) and the mixture was heated to reflux overnight and concentrated. The residue was purified by flash chromatography. Eluting with 5% (v) methanol in dichloromethane gave the desired product 22. $^1$H NMR (400 MHz, acetone-$d_6$): δ6.19 (br s, 1H), 3.51 (q, 2H), 3.05 (t, 2H), 2.30 (s, 3H), 1.39 (s, 9H). This compound was then treated with 30% (v) TFA in dichloromethane for 1 hour and concentrated to give the TFA salt of amine 23 (400 mg). $^1$H NMR (400 MHz, acetone-$d_6$): δ4.40 (t, 2H), 3.51 (t, 2H), 2.29 (s, 3H). This salt was first treated with Amberlite IRA-96® to remove the trifluoroacetic acid and then processed to the final compound as described.

Several other non-limiting examples of amines (representing R$^1$ in formula I) used to react with bromide 13 are listed in Table 2. These amines can either be purchased from commercial sources or can be prepared using routine methods.

TABLE 2

Examples of amines representing R$^1$ in formula I.

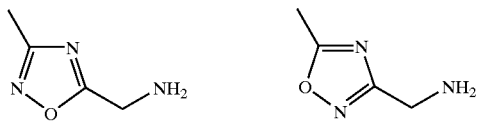

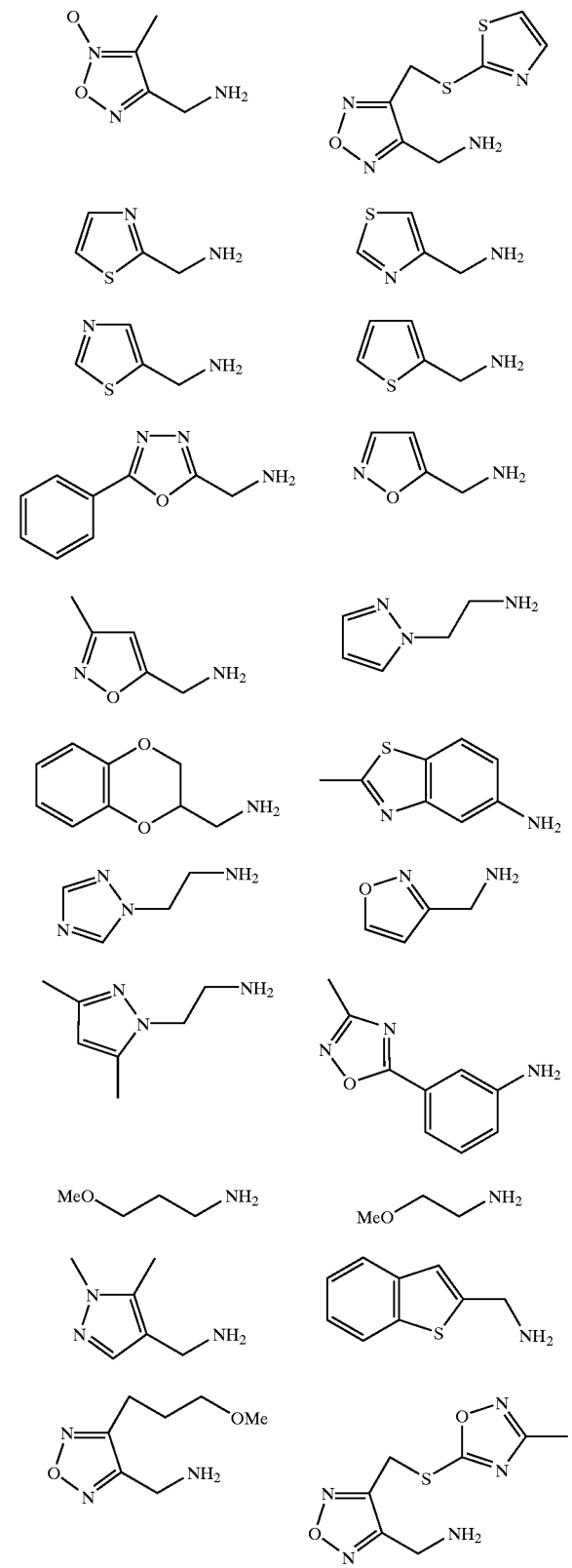

TABLE 2-continued

Examples of amines representing R¹ in formula I.

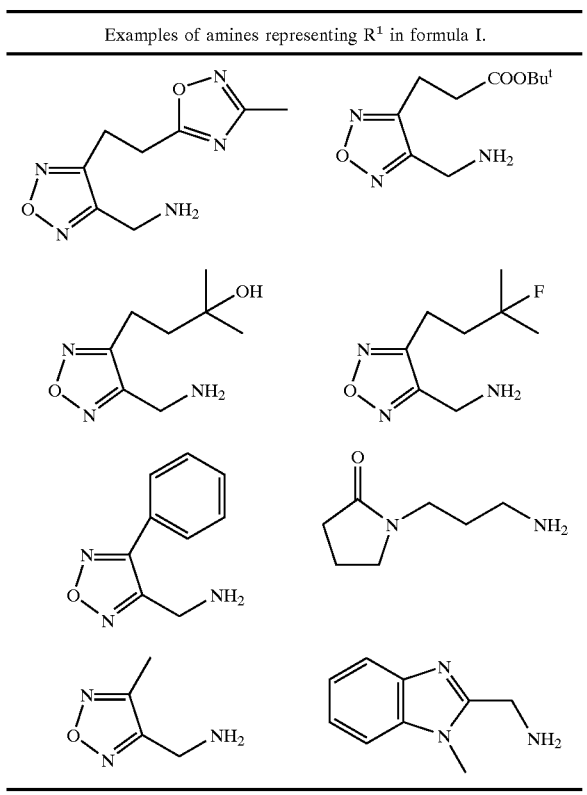

Example 1

(3S)-5-(benzylsulfanyl)-3-{[(2S)-2-(3-{[(4-methyl-1,2,5-oxadiazol-3-yl)methyl]amino}-2-oxo-1,2-dihydro-1-pyrazinyl)butanoyl]amino}-4-oxopentanoic acid

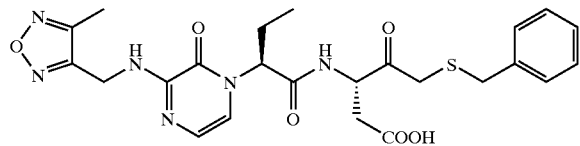

Step 1: t-Butyl (3S)-5-bromo-3-[(9H-9-fluorenylmethoxy)carbonyl]amino-4-oxopentanoate (1)

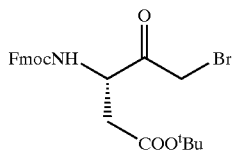

To a solution of N-Fmoc-L-aspartic acid β-tert-butyl ester (21.0 g, 51.0 mmol) in 300 mL of THF at −78° C. was added NMM (7.9 mL, 71.4 mmol) followed by IBCF (8.6 mL, 66.3 mmol). After stirring for 30 minutes at −78° C., this mixture was warmed to −15° C. for 15 minutes. To the mixture was then added twice, in a 10 minutes interval, a solution of diazomethane in ether (1 M, 40 mL) with stirring. The mixture was allowed to warm to 0° C. and to it was added another 60 mL of the diazomethane solution. The solution was then warmed to room temperature and stirred for 10 minutes, recooled back to 0° C. and treated with a solution of HBr(48% aqueous)/AcOH (1/1, v/v, 100 mL) for 5 minutes, diluted with ethyl acetate and water. The organic phase was separated, washed with water and brine, dried over magnesium sulfate, filtered and concentrated. The crude product was purified by flash chromatography. Eluting with hexanes/ethyl acetate (3:1) afforded the desired product as a white powder (20 g, 81% yield). ¹H NMR (400 MHz, acetone-d₆): δ7.85 (d, 2H), 7.69 (d, 2H), 7.41 (t, 2H), 7.32 (t, 2H), 7.02 (bd, 1H, NH), 4.70 (dd, 1H), 4.51–4.41 (m, 2H), 4.38–4.30 (2×d, 2H), 4.25 (t, 1H), 2.85 (dd, 1H), 2.70 (dd, 1H), 1.41 (s, 9H).

Step 2: Preparation of Resin A

A suspension of amino-Merrified resin (Novabiochem, 30 grams, 31.2 mmol), acid 4 (14.7 g, 46.8 mmol), EDCI (10.77 g, 56.12 mmol) and HOBT (8.6 g, 56.16 mmol) in DMF (240 mL) was shaken on an orbital shaker at 190 rpm overnight. The mixture was filtered and the residual resin washed sequentially with DMF, methanol, dichloromethane and methanol and dried under vacuum. The resin then was suspended in a solution of TFA/dichloromethane (1:2, 300 mL) and shaken for 2 h on an orbital shaker. The suspension was filtered, washed with dichloromethane (5×) and methanol (5×) and then dried under vacuum overnight to yield resin A (40.5 g, 0.81 mmol/g).

Step 3: Loading of Ketone 1 to Resin A

A suspension of ketone 1 (4.5 g, 9.22 mmol) and resin A (8.8 g, 7.13 mmol) in THF (70 mL) in the presence of AcOH (0.2 mL, 3.4 mmol) was shaken on an orbital shaker at 200 rpm overnight. The suspension was filtered and residual resin was washed sequentially with THF, dichloromethane, ethyl acetate and diethyl ether. Drying under high vacuum afforded resin B (11.7 g).

Step 4: Preparation of Resin D

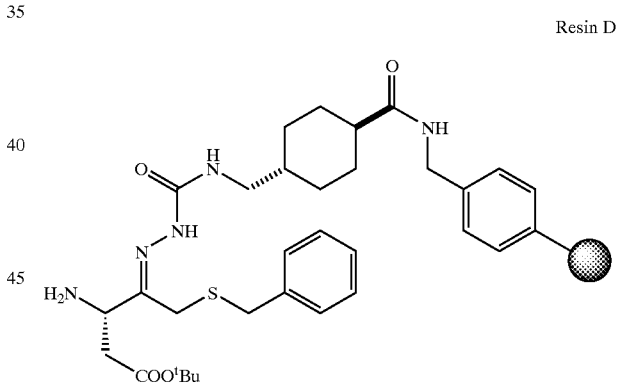

Resin D

To a suspension of resin B (1.6 g) in DMF (6 mL) in a fritted reservoir was added a solution of benzylmercaptan (5.5 mL, 1 M in DMF) and DIEA and the mixture was rotated on a disc (Glas-Col®) for 3 h and filtered. The resin was washed with DMF and then subjected to a solution of 20% piperidine in DMF for 20 minutes and then washed sequentially with DMF, methanol, dichloromethane and methanol and dried under high vacuum to afford resin D.

Step 5. Preparation of Acid 8

A) Preparation of compound 9: To a solution of ethyl (S)-2-aminobutyrate hydrochloride (8.3 g, 49.8 mmol) in dichloromethane was added triethylamine (15 mL) at room temperature and the mixture was cooled to −20° C. To the mixture was added ethyl oxalyl chloride (5.8 mL, 52 mmol) dropwise in 30 min and suspension was allowed to warm slowly to room temperature and stirred for five additional hours. The mixture was diluted with water and the organic layer was washed with water (2×) and brine, dried over MgSO$_4$ and filtered. The filtrate was concentrated in vacuo to afford product 9 as a yellowish oil (11.6 g). $^1$H NMR (400 MHz, acetone-d$_6$): δ8.15 (br s, 1H, NH), 4.38 (m, 1H), 4.29 (q, 2H), 4.16 (m, 2H), 1.93 (m, 1H), 1.82 (m, 1H), 1.30 (t, 3H), 1.23 (t, 3H), 0.94 (t, 3H).

Scheme for the Preparation of Pyrazinone Acid 8

C) Preparation of aldehyde 11: A solution of acetal 10 (68 g) in THF (400 mL) and 1N HCl (100 mL) was heated to reflux for 3 hours and cooled to room temperature. The solution was diluted with water and extracted with ethyl acetate (3×). The extracts were combined, washed with brine, dried over MgSO$_4$, filtered and concentrated. The crude product was purified by recrystallization from ethyl acetate and hexanes. Two crops of aldehyde 11 (47 g) was

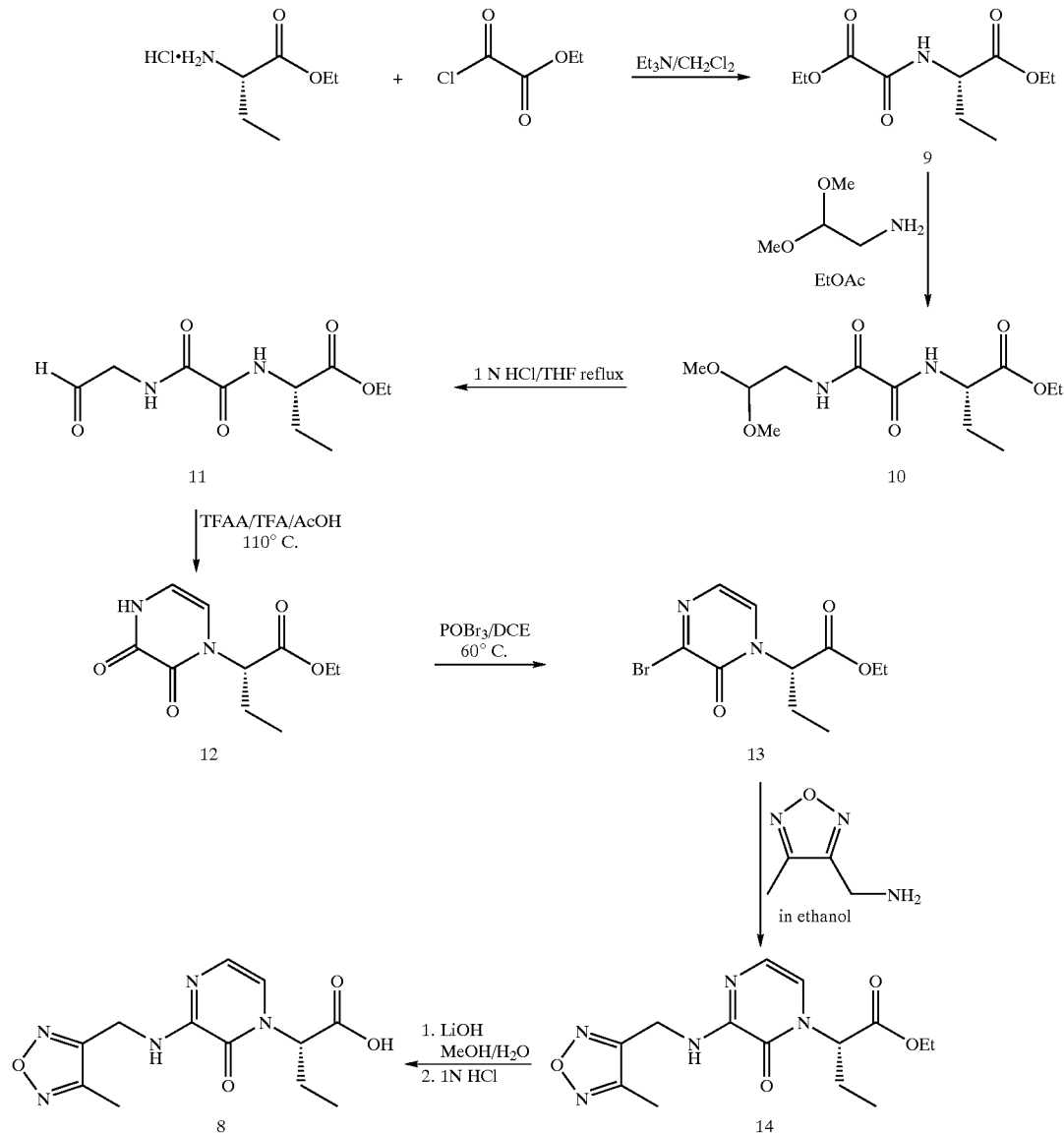

obtained as a light yellow solid. $^1$H NMR (500 MHz, acetone-d$_6$): δ9.62 (s, 1H), 8.46 (br s, 1H, NH), 8.13 (br s, 1H, NH), 4.38 (m, 1H), 4.22–4.12 (m, 4H), 2.00–1.80 (m, 2H), 1.24 (t, 3H), 0.94 (t,3H).

B) Preparation of acetal 10: A solution of compound 9 (108.5 g, 470 mmol) and aminoacetaldehyde dimethyl acetal (54 mL, 490 mmol) in ethyl acetate was heated to 60° C. for three hours and to the solution was added hexanes. The mixture was cooled to room temperature and the white solid was collected upon vacuum filtration. Drying under high vacuum afforded acetal 10 as a white powder (110 g). $^1$H NMR (300 MHz, acetone-d$_6$): δ8.20 (br s, 1H, NH), 8.00 (br s, 1H, NH), 4.53 (t, 1H), 4.35 (m, 1H), 4.17 (m, 2H), 3.42 (m, 2H), 3.30 (s, 6H), 2.00–1.80 (m, 2H), 1.24 (t, 3H), 0.94 (t, 3H).

D) Preparation of compounds 12: To a solution of aldehyde 11 (35 g, 143 mmol) in acetic acid (88 mL) was added TFAA (22 mL, 157 mmol) and TFA (12 mL, 157 mmol) and the mixture was heated to 110° C. for 5 hours and cooled to room temperature. The black mixture was concentrated in vacuo and the residue purified by flash column chromatography. Eluting with 5% methanol in dichloromethane furnished compound 12 (32 g) as a dark thick liquid. $^1$H NMR (400 MH, acetone-d6): δ10.45 (br s, 1H), 6.48 (s, 2H), 5.08 (dd, 1H), 4.15 (q, 2H), 2.20 (m, 1), 2.03 (m, 1H), 1.20 (t, 3H), 0.92 (3H).

E) Preparation of bromide 13: To a solution of compound 12 (30 g, 132.7 mmol) in dichloroethane (500 mL) was added phosphorus oxybromide (42 g) and the mixture was heated to 60° C. overnight and cooled to 0° C. To the black mixture was added solid sodium hydrogen phosphate and water with vigorous stirring. After all solid was dissolved, the solution was further treated with a solution of saturated sodium bicarbonate until gas evolution ceased. The mixture was then extracted with dichloromethane (3×). The extracts were combined, washed with water and brine, dried over MgSO$_4$, filtered and concentrated. The residue was purified by flash column chromatography. Eluting with 50% (v) ethyl acetate in hexanes gave bromide 13 as a light yellow viscous oil (22.5 g). $^1$H NMR (300 MHz, acetone-d$_6$): δ7.64 (d, 1H), 7.22 (d, 1H), 5.18 (dd, 1H), 4.18 (q, 2H), 2.35–2.15 (m, 2H), 1.22 (t, 3H), 0.93 (t, 3H). [α]$_D$ 50° (MeOH).

F) Preparation of acid 8: A solution of bromide 13(3.5 g) and 3-aminomethyl-4-methylfurazan (2.74 g) in ethanol was heated to reflux overnight and cooled to room temperature. The mixture was concentrated and the residue was purified by flash chromatography. Eluting with ethyl acetate/hexanes (2:1 v/v) afforded the desired product 14 (2.75 g). $^1$H NMR (400 MHz, acetone-d$_6$): δ7.28 (br s, 1H, NH), 6.82 (d, 1H), 6.76 (d, 1H), 5.18 (dd, 1H), 4.80 (d, 2H), 4.14 (q, 2H), 2.41 (s, 3H), 2.25–2.18 (m, 1H), 2.09–2.00 (m, 1H), 1.19 (t, 3H), 0.87 (t, 3H). The ethyl ester in 14 was hydrolyzed as follow: To a solution of ester 14 (2.75 g) in MeOH was added 1N LiOH in water (8.6 mL) at 0° C. and the solution was stirred overnight and concentrated. The residue was diluted with 1N HCl and ethyl acetate. The organic layer was separated, washed with brine, dried over sodium sulfate and filtered. Concentration in vacuo afforded acid 8 as a light yellow solid (2.6 g). $^1$H NMR (400 MHz, acetone-d$_6$): δ7.42 (br s, 1H, NH), 6.85 (d, 1H), 6.78 (d, 1H), 5.21 (dd, 1H), 4.80 (d, 2H), 2.39 (s, 3H), 2.30–2.19 (m, 1H), 2.11–2.03 (m, 1H), 0.88 (t, 3H).

Step 6. Title Compound

To a suspension of resin D (90 mg, 0.5 mmol/g) in DMP in a fritted reservoir was added acid 8 (42 mg) and DIEA (39 μL), and the mixture was rotated on a Glas-Col® rotor for 3 hours and filtered. The residual resin was washed with DMF, MeOH, THF, MeOH, ethyl acetate and diethyl ether and then treated with a cocktail consisting of TFA and water (9:1 v/v) for 1 h. The mixture was filtered and the filtrate was collected. The residual resin was then washed with dichloromethane and acetonitrile. The filtrate and washing solutions were combined, concentrated in vacuo and triturated with ether to afford the title compound as a white powdery solid. $^1$H NMR (400 MHz, acetone-d$_6$): δ9.41 (br s, 1H), 8.20 (br s, 1H), 7.34–7.28 (m, 4H), 7.22–7.19 (m, 2H), 7.00 (d, 1H), 5.41 (dd, 1H), 5.12 (d, 2H), 5.05–4.98 (m, 1H), 3.69 (s, 2H), 3.39 (dd, 2H), 2.89 (dd, 1H), 2.78 (dd, 1H), 2.42 (s, 3H), 2.29–2.18 (m,1H), 2.07–1.98 (m, 1H), 0.93 (t, 3H). m/z (−ESI): 527.1 (M−1)$^-$.

Example 2

(3S)-5-(benzylsulfanyl)-3-{[(2S)-2-(3-{[3-(3-methyl-1,2,4-oxadiazol-5-yl)-propan-1-yl]amino}-2-oxo-1,2-dihydro-1-pyrazinyl)butanoyl]amino}-4-oxopentanoic acid

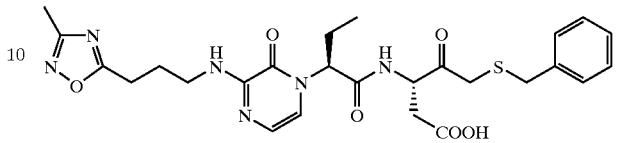

Step 1. Preparation of 3-(3-methyl-1,2,4-oxadiaol-5-yl)-propylamine (15)

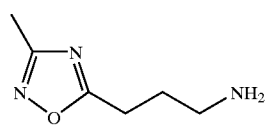

15

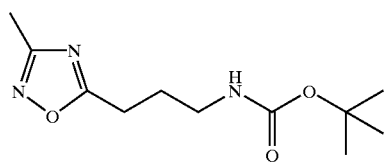

16

To a solution of 4-t-butoxycarbonylamino-butyric acid (4 g) in DME was added EDCI (5.7 g), DMAP (0.48 g) and methylamidoxime (1.45 g) was heated to 80° C. for 3 days and cooled to room temperature. After concentration the mixture was purified by flash chromatography. Eluting with 4% methanol in dichloromthane afforded compound 16 (1.1 g). $^1$H NMR (400 MHz, acetone-d$_6$): δ6.11 (br s, 1H), 3.18 (1, 2H), 2.89 (t, 2H), 2.28 (s, 3H), 1.93 (m, 2H), 1.39 (s, 9H). The Boc group in 16 was deprotected with TFA in dichloromethane. Thus 16 (1.1 g) was stirred with TFA/dichloromethane (1/1, v/v) for 5 hours and concentrated. To the mixture was then added aqueous Na$_2$CO$_3$ and the volatiles were removed under reduced pressure and the solid residue treated with ethanol and then filtered. The filtrate was concentrated to afford the desired amine 15 (0.6 g) as a colorless oil. $^1$H NMR (400 MHz, CD$_3$OD): δ3.25 (t, 2H), 2.91 (t, 2H), 2.25 (s, 3H), 2.01 (qt, 2H).

Step 2. Preparation of Compound 17

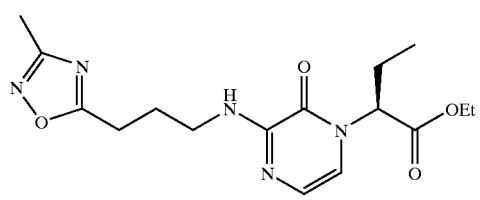

17

A solution of amine 15 (340 mg) and bromide 13 (174 mg) in ethanol was heated to reflux overnight and then diluted with water and ethyl acetate. The layers were separated and the aqueous layer was extracted with ethyl acetate (2x). The organic layers were combined, washed with brine, dried over MgSO₄ and filtered. The filtrate was concentrated and the residue was purified by flash chromatography. Eluting with 50–80% (v) ethyl acetate in hexanes afforded the desired product 17 (74 mg) as a colorless liquid. $^1$H NMR (400 MHz, acetone-d$_6$): δ6.83 (br s, 1H), 6.80 (d, 1H), 6.67 (d, 1H), 5.13 (dd, 1H), 4.13 (q, 2H), 3.54 (dd, 2H), 2.95 (t, 2H), 2.28 (s, 3H), 2.25–2.00 (m, 4H), 1.20 (t, 3H), 0.87 (t, 3H).

To a solution of the ethyl ester 17 (74 mg) in MeOH (3 mL) and water (1 mL) was added LiOH monohydrate (11 mg) and the mixture was stirred at room temperature overnight and acidified with 1N HCl until pH~1. The mixture was concentrated to dryness and the white solid thus obtained was used directly for the following transformation.

Step 3. The Title Compound

To a suspension of resin D (100 mg, 0.6 mmol/g) in DMF in a fritted reservoir was added the acid from above (35 mg), HATU (38 mg) and DIEA (17 μL) and the mixture was rotated at room temperature for 3 hours and filtered. The resin was washed sequentially with DMF (3x), MeOH (3x), THF (3x), MeOH, ethyl acetate (3x) and ether (3x) and then treated with a cocktail of TFA/H2O (9/1, v/v) for 1.5 hours and filtered. The filtrate was collected and the resin washed with dichloromethane and acetonitrile. The filtrate and washing solutions were combined and concentrated. The residue was triturated with ether to give the title compound as a light yellow solid (19 mg). m/z (+APCI): 555.4 (M+1)$^+$.

Example 3

(3S)-5-(benzylsulfanyl)-3-{[(2S)-2-(3-{[2-oxo-pyrrolidin-1-yl)-propan-1-yl]amino}-2-oxo-1,2-dihydro-1-pyrazinyl)butanoyl]amino}-4-oxopentanoic acid

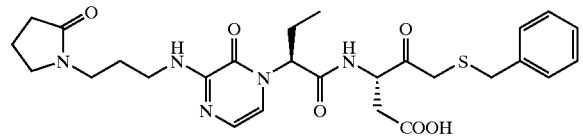

Step 1. Preparation of acid 19

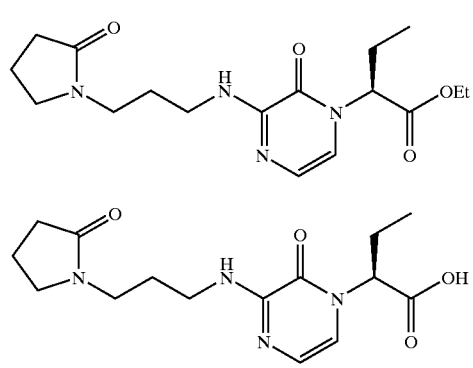

A solution of bromide 13 (100 mg) and 1-(3-aminopropyl)-2-pyrrolidinone (113 mg) in ethanol was heated to reflux overnight and concentrated. The residue was purified by flash chromatography. Eluting with 20% (v) methanol in dichloromethane yielded the desired product 18 (113 mg). $^1$H NMR (400 MHz, acetone-d$_6$): δ6.90 (br s, 1H), 6.78 (d, 1H), 6.67 (d, 1H), 5.13 (dd, 1H), 4.13 (q, 2H), 3.543.45–3.25 (m, 7H), 2.27–1.95 (m, 6H), 1.80 (m, 2H), 1.20 (t, 3H), 0.87 (t, 3H).

To a solution of 18 (113 mg) in MeOH (3 mL) and water (1 mL) was added LiOH monohydrate (16 mg) and the mixture was stirred at room temperature for 2 hours and then acidified with 1N HCl. The mixture was then concentrated to dryness to furnish acid 19 which was used directly without further purification.

Step 2. the Title Compound

To a suspension of resin D (114 mg, 0.7 mmol/g) in DMF in a fritted reservoir was added acid 19 (60 mg) from above, HATU (61 mg) and DIEA (28 μL) and the mixture was rotated at room temperature for 2 hours and filtered. The resin was washed sequentially with DMF (3x), MeOH (3x), THF (3x), MeOH, ethyl acetate (3x) and ether (3x) and then treated with a cocktail of TFA/H2O (9/1, v/v) for 1 hour and filtered. The filtrate was collected and the resin washed with dichloromethane and acetonitrile. The filtrate and washing solutions were combined and concentrated. The residue was triturated with ether to give the title compound as a light yellow solid (35 mg). m/z (−APCI): 556.4 (M−1)$^−$.

Compounds 2, 5–10 and 18–28 of table 1 were synthesized in a similar manner. The corresponding amines were reacted with bromide 13 and the individual reaction products were processed accordingly to provide the compounds of table 1.

Example 4

(3S)-3-{[(2S)-2-(3-{[(4-Methyl-1,2,5-oxadiazol-3-yl)methyl]amino}-2-oxo-1,2-dihydro-1-pyrazinyl)butanoyl]amino}-4-oxo-5-tetrahyrdo-1H-pyrrolylpentanoic acid

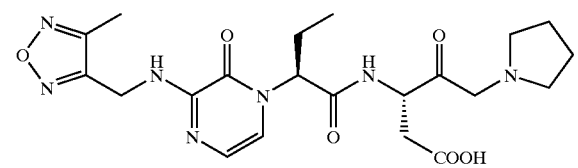

The title compound was synthesized in accordance with the following scheme.

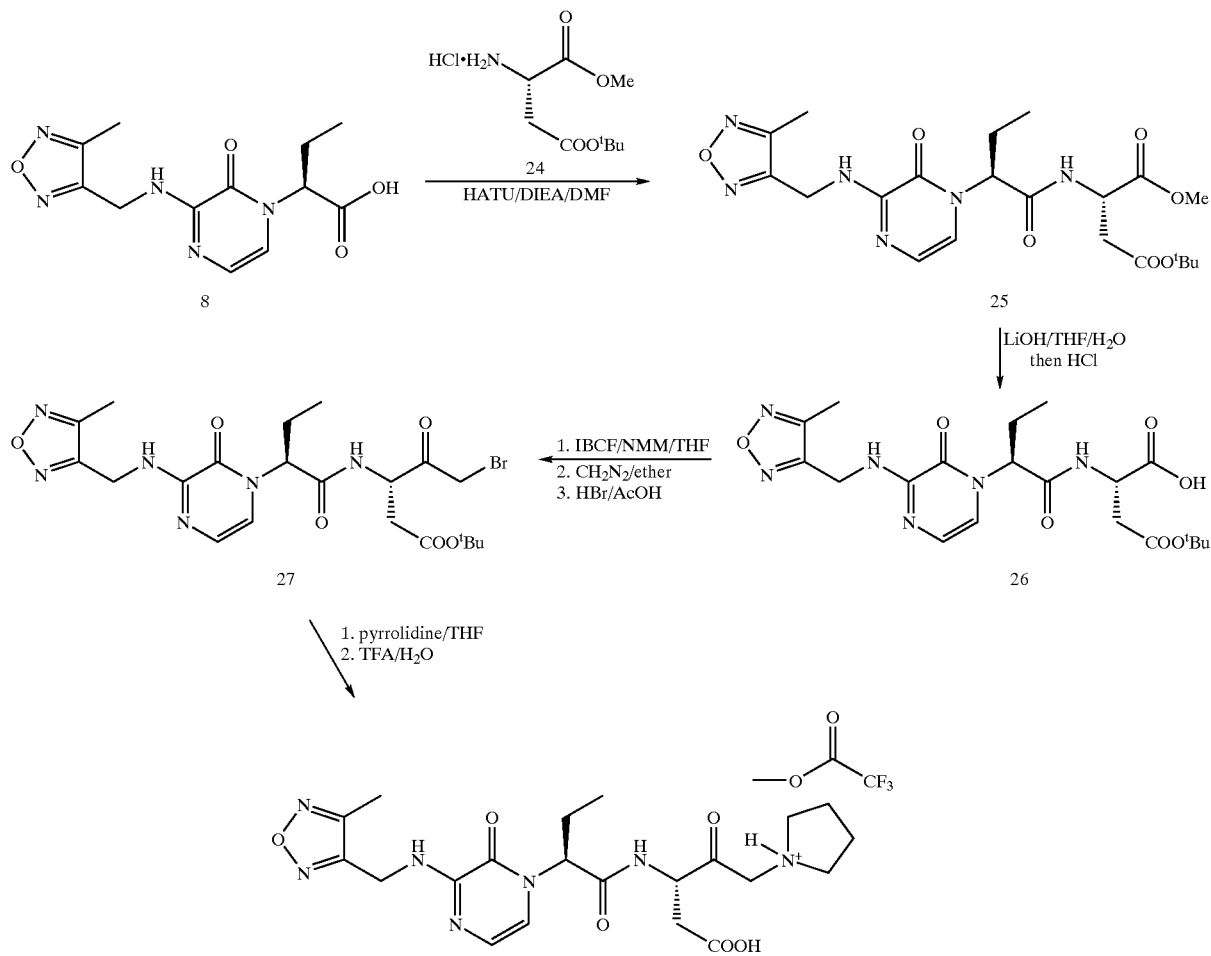

Example 4

Step 1. Preparation of Acid 26

To a solution of pyrazinone acid 8 (1.07 g) in DMF was added sequentially β-t-butyl aspartic acid methyl ester hydrochloride (24) (0.96 g), HATU (1.53 g) and DIEA (1.6 mL) and the mixture was stirred at room temperature for 4 hours. The mixture was then diluted with water and diethyl ether and the organic layer was separated. The aqueous layer was extracted with ether (3×) and the organic layer and organic extracts were combined, washed with water (2×) and brine, dried over $MgSO_4$ and filtered. The filtrate was concentrated in vacuo to yield the desired ester 25 (1.6 g). $^1$H NMR (400 MHz, acetone-$d_6$): δ7.83 (br s, 1H), 7.29 (br s, 1H), 6.88 (d, 1H), 6.79 (d, 1H), 5.39 (dd, 1H), 4.81–4.70 (m, 3H), 3.67 (s, 3H), 2.72 –2.68 (m, 2H), 2.40 (s, 3H), 2.20–2.10 (m, 1H), 1.89–1.78 (m, 1H), 1.32 (s, 9H), 0.88 (s, 3H). The methyl ester 25 was hydrolyzed a follow: To a solution of ester 25 (1.6 g) in THF (35 mL) was added 1N aqueous LiOH (3.4 mL) at room temperature and the mixture was stirred for four hours and diluted with 1N HCl and ethyl acetate. The phases were separated and the organic phase was washed with brine, dried over $MgSO_4$ and filtered. The filtrate was concentrated in vacuo to yield acid 26 as a white solid (1.4 g). $^1$H NMR (400 MHz, acetone-$d_6$): δ7.91 (br s, 1H), 7.62 (br s, 1H), 6.96 (d, 1H), 6.85 (d, 1H), 5.50 (dd, 1H), 4.85 (d, 2H), 4.83–4.77 (m, 1H), 2.76–2.73 (m, 2H), 2.40 (s, 3H), 2.20–2.10 (m, 1H), 1.92–1.83 (m, 1H), 1.32 (s, 9H), 0.8 (s, 3H).

Step 2. Preparation of Bromomethyl Ketone 27

To a solution of acid 25 (614 mg, 1.32 mmol) in THF at −78° C. was added NMM (160 μL) followed by IBCF (180 μL). After stirring for 30 minutes at −78° C., this mixture was warmed to −15° C. for 15 minutes. To the mixture was then added twice, in a 10 minutes interval, a solution of diazomethane in ether (1 M) with stirring until a yellow color persisted. The mixture was allowed to warm to 0° C. and to it was added another portion of the diazomethane solution. The solution was then warmed to room temperature and stirred for 10 minutes, recooled back to 0° C. and treated with a solution of HBr (45% aqueous)/AcOH (1/1, v/v, 10 mL) for 5 minutes, diluted with ethyl acetate and water. The organic phase was separated, washed with water and brine, dried over magnesium sulfate, filtered and concentrated. The crude product was purified by flash chromatography. Eluting with hexanes/ethyl acetate (2:1) afforded the desired product 27 (520 mg). $^1$H NMR (400 MHz, acetone-$d_6$): δ8.08 (br s, 1H), 7.29 (br s, 1H), 6.87 (d, 1H), 6.81 (d, 1H), 5.29 (dd, 1H), 4.91–4.86 (m, 1H), 4.79 (d, 2H), 4.38 (dd, 2H), 4.05 (dd, 2H), 2.85 (dd, 1H), 2.68 (dd, 1H), 2.41 (s, 3H), 2.22–2.15 (m, 1H), 1.99–1.90 (m, 1H), 1.35 (s, 9H), 0.89 (t, 3H).

Step 3. Title Compound

To a solution of 27 (175 mg) in THF (5 mL) was added pyrrolidine (30 μL) and the mixture was stirred at room temperature overnight. After concentration, the residue was purified by flash chromatography. Eluting with 5%MeOH in dichloromethane afforded the desired product (144 mg). $^1$H NMR (400 MHz, acetone-d$_6$): δ7.90 (br s, 1H), 7.30 (br s, 1H), 6.88 (d, 1H), 6.83 (d, 1H), 5.33 (dd, 1H), 4.83–4.75 (m, 3H), 3.50 (d, 1H), 3.35 (d, 1H), 2.80 (dd, 1H), 2.69 (dd, 1H), 2.59–2.40 (m, 4H), 2.30 (s, 3H), 2.20–2.11 (m, 1H), 1.94–1.85 (m, 1H), 1.35 (s, 9H), 0.88 (t, 3H). The t-butyl ester was cleaved with TFA in dichloromethane (1:1, v/v) for 1 hour at room temperature and the mixture was concentrated. The residue was triturated with diethyl ether to give the title compound as a white solid (140 mg) in the form of a TFA salt. $^1$H NMR (400 MHz, acetone-d$_6$): δ8.32 (br s, 1H), 7.71 (br s, 1H), 6.93 (d, 1H), 6.89 (d, 1H), 5.12 (dd, 1H), 4.83 (d, 2H), 4.84–4.76 (m, 1H), 4.68 (dd, 1H), 4.56 (dd, 1H), 3.95–3.83 (m, 2H), 3.88–3.19 (m, 2H), 2.94 (dd, 1H), 2.84 (dd, 1H), 2.42 (s, 3H), 2.26–2.10 (m, 5H), 0.90 (t, 3H). m/z (−ESI): 527.1 (M−1)$^-$.

Compounds 12–16 and 32–42 of table 1 were prepared similarly.

Example 5

(3S)-3-{[(2S)-2-(3-{[(4-methyl-1,2,5-oxadiazol-3-yl)methyl]amino}-2-oxo-1,2-dihydro-1-pyrazinyl) butanoyl]amino}-4-oxopentanoic acid

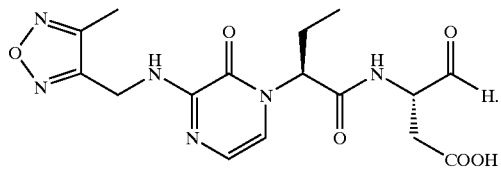

Step 1: t-Butyl (3S)-3-[(9H-9-fluorenylmethoxy)carbonyl] amino-4-oxybutanoate (29) and Resin E a) To a solution of N-Fmoc-L-aspartic acid β-t-butyl ester (19.0 g, 46.2 mmol) in 300 mL of tetrahydrofuran (TH) at −78° C. was added N-methyl morpholine (NMM, 5.9 mL, 53.3 mmol) followed by IBCF (6.9 mL, 53.3 mmol). After 10 minutes this mixture was warmed to 0° C. for 40 minutes and then recooled to −78° C. A suspension of sodium borohydride (3.85 g, 102 mmol) in 25 mL of methanol was added and the mixture was stirred at −78° C. for 2 h. The reaction was quenched into 400 mL saturated aqueous ammonium chloride and extracted with ethyl acetate (4×100 mL). The combined organic layers were washed with brine and dried over anhydrous magnesium sulfate, filtered and concentrated. The residue was purified on silica gel (50% ethyl acetate/hexane) to give the desired product 28: $^1$H NMR (400 MHz, acetone-d$_6$) δ7.85 (d, 2H,), 7.67 (d, 2H), 7.40 (t, 2H), 7.30 (t, 2H), 6.32 (br, d, 1H), 4.40–4.15 (m, 3H), 4.10–3.98 (m, 1H), 3.92 (t, 1H), 3.65–3.48 (m, 2H), 2.60 (dd, 1H,), 2.41 (dd, 1H), 1.40 (5, 9H).

b) Oxalyl chloride (960 μL, 11 mmol) was added to a solution of DMSO (852 μL, 12 mmol) in 50 mL CH$_2$Cl$_2$ at −78° C. The resulting mixture was stirred at −78° C. for 30 minutes and the N-Fmoc-β-t-butyl aspartic alcohol (28) (3.98 g, 10 mmol) in CH$_2$Cl$_2$ (15 mL) was added dropwise. The mixture was stirred at −78° C. for 1 h, then i-Pr$_2$NEt (5.20 mL, 30 mmol) was added dropwise. The resulting mixture was stirred at −78° C. for 50 min and at 0° C. for 25 min. The mixture concentrated and then partitioned between ether and H$_2$O. The ether layer was washed with water, brine, dried over MgSO$_4$ and filtered. The filtrate was concentrated to give crude aldehyde 29 which was reacted directly with resin A to afford resin E as described for resin D without purification.

Step 2. The Title compound.

Resin E (900 mg, 0.45 mmol/g) was first treated with 10 mL of 20% (v) piperidine in DMF for 10 minute and then washed thoroughly with DME, MeOH, THF and ethyl acetate and dried under vacuum. This resin was suspended

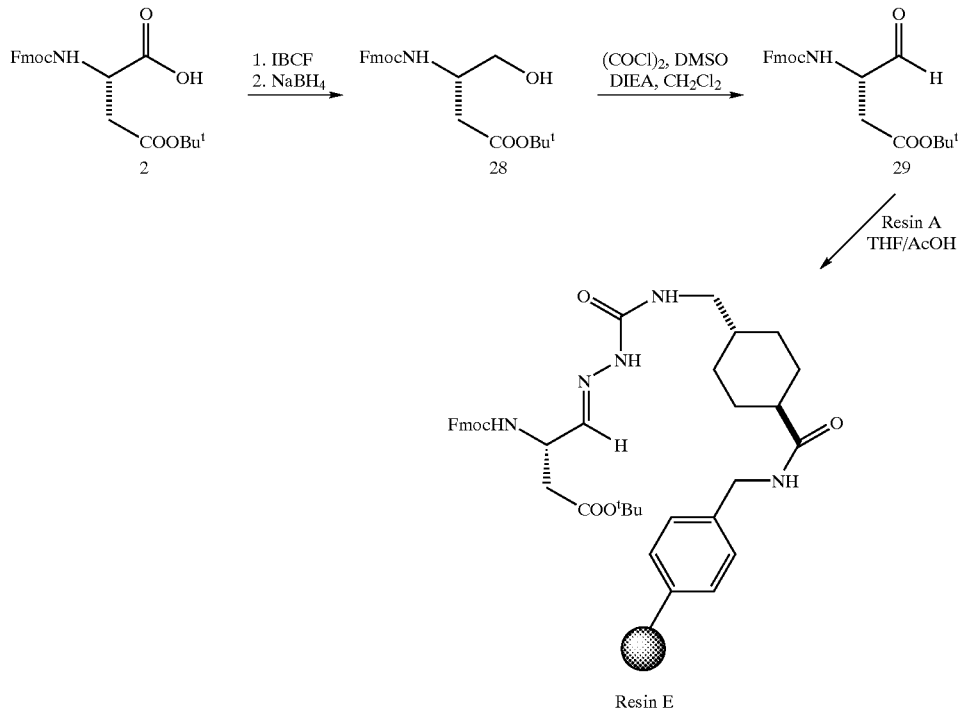

in DMF and to the suspension was added acid 8 (237 mg), HATU (308 mg) and DIEA (141 μL) and the mixture was agitated for 2 hours and filtered. The resin was washed sequentially with DMF, MeOH, THF, MeOH, ethyl acetate and ether and dried under high vacuum. The dried resin was then treated with a cocktail consisting TFA/H$_2$O (9/1, v/v) for 2 hours and filtered. The resin was washed with acetonitrile and washing solutions were combined with the filtrate, concentrated in vacuo and the residue was purified by flash chromatography. Eluting with 10% (v) methanol in dichloromethane afforded the title compound which existed as a mixture of hemiacetals in acetone-d$_6$. $^1$H NMR (400 MHz, acetone-d$_6$): δ8.10 (br s, 1H), 7.69 (br s, 1H), 6.99 (d, 1H), 6.85 (d, 1H), 5.35 (dd, 1H), 4.88 (d, 2H), 4.33–4.22 (m 1H), 3.01–2.91 (m, 1H), 2.71 (dd, 1H), 2.50 (dd, 1H), 2.41 (s, 3H), 2.21–2.12 (m, 1H), 1.97–1.86 (m, 1H), 0.88 (t, 3H). m/z (–ESI): 391.5 (M–1)$^-$.

Assays for Determining Biological Activity

1. Measurement of Caspase Activity by Cleavage of a Fluorogenic Substrate

A fluorogenic derivative of the tetrapeptide recognized by caspase-3 and corresponding to the P$_1$ to P$_4$ amino acids of the PARP cleavage site, Ac-DEVD-AMC (AMC, amino-4-methylcoumarin) was prepared as follows: i) synthesis of N-Ac-Asp(OBn)-Glu(OBn)-Val-CO$_2$H, ii) coupling with Asp(OBn)-7-amino-4-methylcoumarin, iii) removal of benzyl groups.

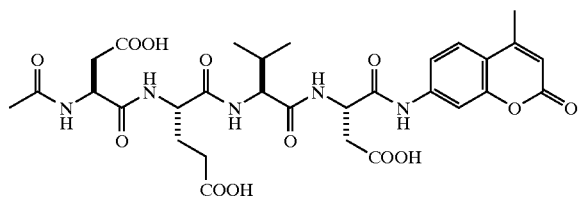

Standard reaction mixtures (300 μL final volume), contained Ac-DEVD-AMC and purified or crude caspase-3 enzyme in 50 mM Hepes/KOH (pH 7.0), 10% (v/v) glycerol, 0.1% (w/v) CHAPS, 2 mM EDTA, 5 mM dithiothreitol, and were incubated at 25° C. Reactions were monitored continuously in a spectrofluorometer at an excitation wavelength of 380 nm and an emission wavelength of 460 nm.

2. Cell Death Detection ELISA (Whole Cell Assay)

Photometric immunoassay for the qualitative and quantitative in vitro determination of cytoplasmic histone-associated-DNA-fragments (mono- and oligonucleosomes) after induced cell death. This assay was performed using the commercially available kit from Boehringer Mannheim, cat. No. 1 920 685.

3. In Vivo Myocardial Ischemia and Reperfusion Injury in Rats

Male Sprague-Dawley rats (300–400 g) were fasted overnight, and then anesthetized with intraperitoneal administration of sodium pentobarbital (65 mg/kg). To monitor heart rate and aortic pressure the left carotid artery was isolated and a cannula placed in the vessel. The aortic cannula was interfaced with a pressure transducer which was connected to a physiologic recorder. The left jugular vein was isolated and cannulated for administration of a caspase inhibitor compound or vehicle (2% dimethylsulfoxide in 0.9% NaCl). A left thoracotomy was performed in the region overlying the heart and the pericardium opened, exposing the heart. The origin of the left coronary artery was visualized and a 4.0 suture passed under the artery approximately 2–3 mm from its origin. The ends of the suture were passed through a short length of 2 mm id tubing and coronary artery occlusion effected by placing tension on the suture such that the tube compressed the artery. After initial placement of the suture/occluder, the thoracotomy was closed with a small clamp and opened only to effect occlusion and reperfusion of the artery. A Lead II electrocardiograph (ECG) signal was obtained by placing subdermal platinum leads and continuously monitored. After a baseline period of 20–30 minutes the left coronary artery was occluded for 45 minutes. The period of reperfusion was 3 hours. The caspase inhibitor or vehicle was administered as a first bolus 5 minutes before the onset of ischemia and a second bolus was administered again at the onset of reperfusion. Additionally, an infusion was initiated immediately after the first bolus dose. Control animals received the vehicle alone in equal volumes to the caspase inhibitor treated animals. At the end of reperfusion the animals were euthanized and infarct size determined using a dual staining technique (1.5% w/v triphenyltetrazolium chloride to demarcate infarct tissue and 0.25% w/v Evan's blue to demarcate the area at risk of infarct. The heart was subsequently cut transversely into 4 slices of equal thickness, and infarct size and area at risk quantified using planimetry.

Using the above procedure, it is demonstrated that administration of a caspase inhibitor reduces infarct size in the rat subjected to 45 minutes of regional ischemia and 3 hours of reperfusion.

4. In vivo Rat Middle Cerebral Artery Occlusion (MCAO)

Male Wistar rats are anesthetized with isoflurane (1.5% –3%) using a face mask for surgical isolation of the right middle cerebral artery (MCA) and the right and left common carotid artery. Anesthetized animals are then placed on a water jacketed heating pad to maintain normal body temperature. To ensure adequate hydration throughout the experiment, rats are administered 10–15 ml/kg of sterile 0.9% NaCl subcutaneously after anesthesia. The rats are then placed on its right side and the heads immobilized. An incision is made directly in front of the ear, extending down from the base of the ear approximately 1.5 cm. The skin is held back and the salivary gland dissected from surrounding tissues. The gland is pulled forward and down away from surgical field. The temporalis muscle is dissected and retracted. Fascia overlying the skull is removed, leaving a clean section of the skull. The bone of the skull is "thinned" with surgical drill (2 mm burr) and remaining skull dissected away from the dura with forceps. The dura is removed, revealing the MCA. The right MCA is occluded using a 1 mm microclip. The right common carotid artery is permanently occluded using a suture. The left common carotid artery is occluded for a period of time equal to the MCA. Rats are awake within 10 minutes after the end of anesthesia. Analgesis is provided to the rats with oxymorphone (0.01 ml/100 g body weight), once or twice according to veterinary advice.

After surgical isolation of the MCA, the MCA is occluded for a period of 30–120 minutes. The left common carotid artery is occluded for the same period of time as the MCA. In these experiments, compounds are administered by different route (icv, iv or ip), as a bolus and/or continuous infusion, before or after the occlusion. Both the MCA and the left common carotid artery are then reperfused. Animals are then administered prophylactic analgesia, and returned to individual cages. At the end of reperfusion, the animals are euthanized and the brains are cut into 2 mm slices and stained with 1.5% w/v triphenyltetrazolium chloride. The infarct size in the brain is determined using a commercially available imaging system.

Using the above procedure, it is demonstrated that administration of a caspase-3 inhibitor reduces infarct size in the cortex regions of the rat brains when the animals are subjected to a 30 to 90 minutes ischemia and 24 hours of reperfusion.
What is claimed is:
1. A compound in accordance with table 1:
TABLE 1
Compound Number
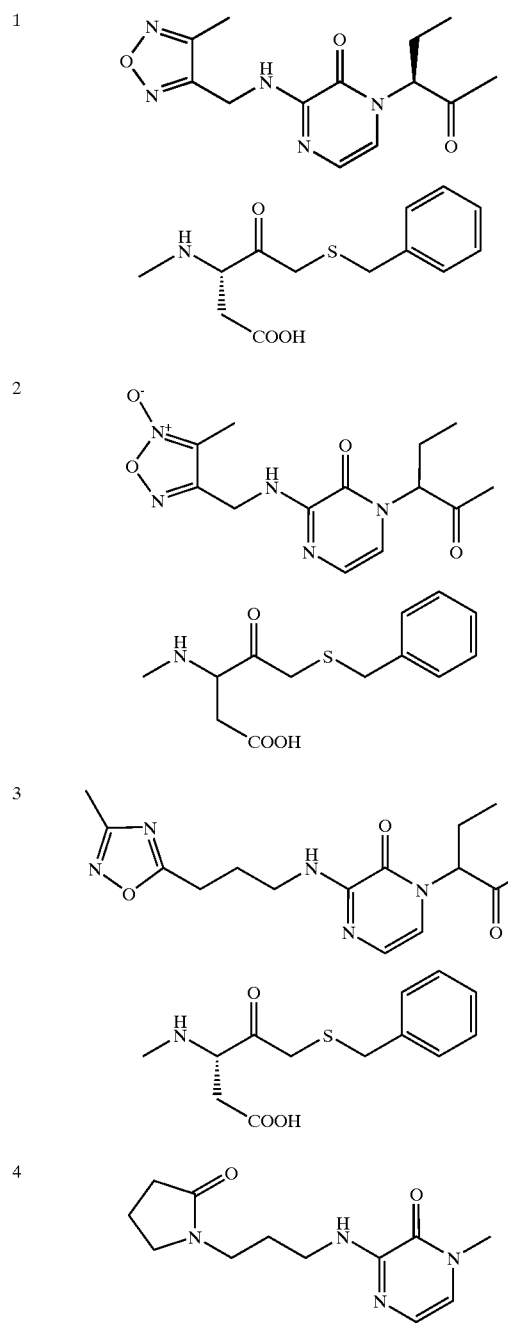
TABLE 1-continued
Compound Number
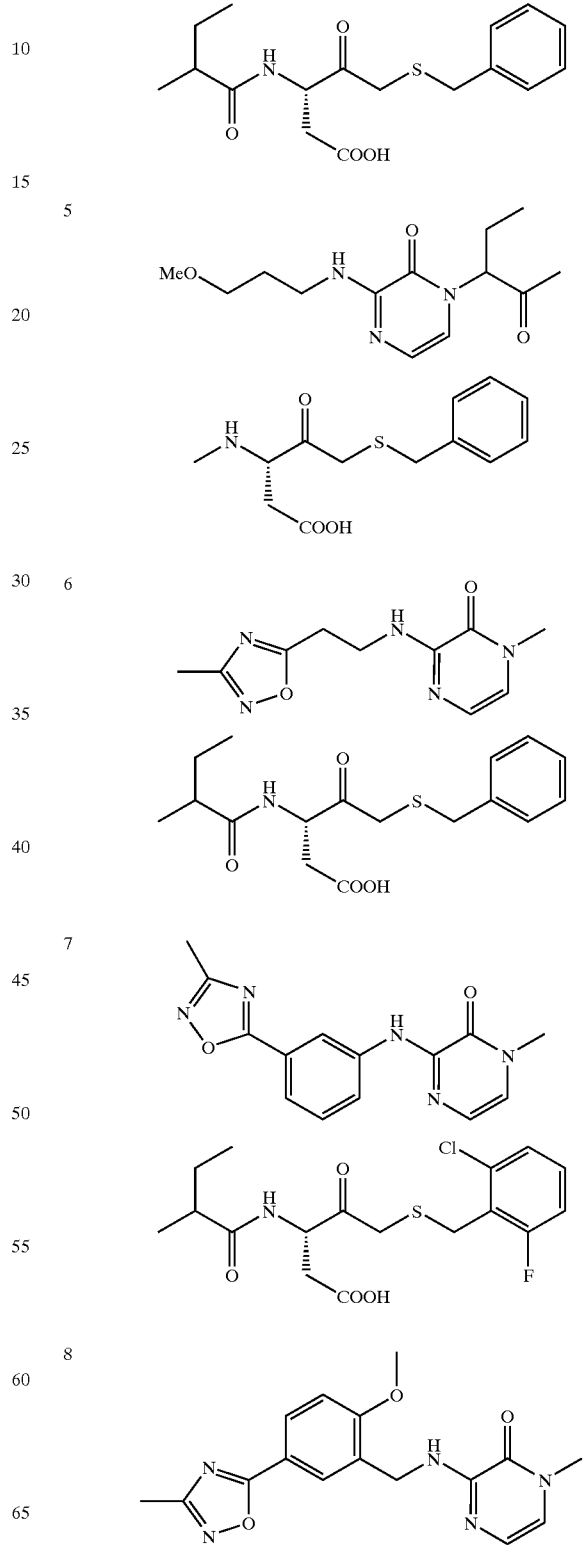

TABLE 1-continued
Compound Number
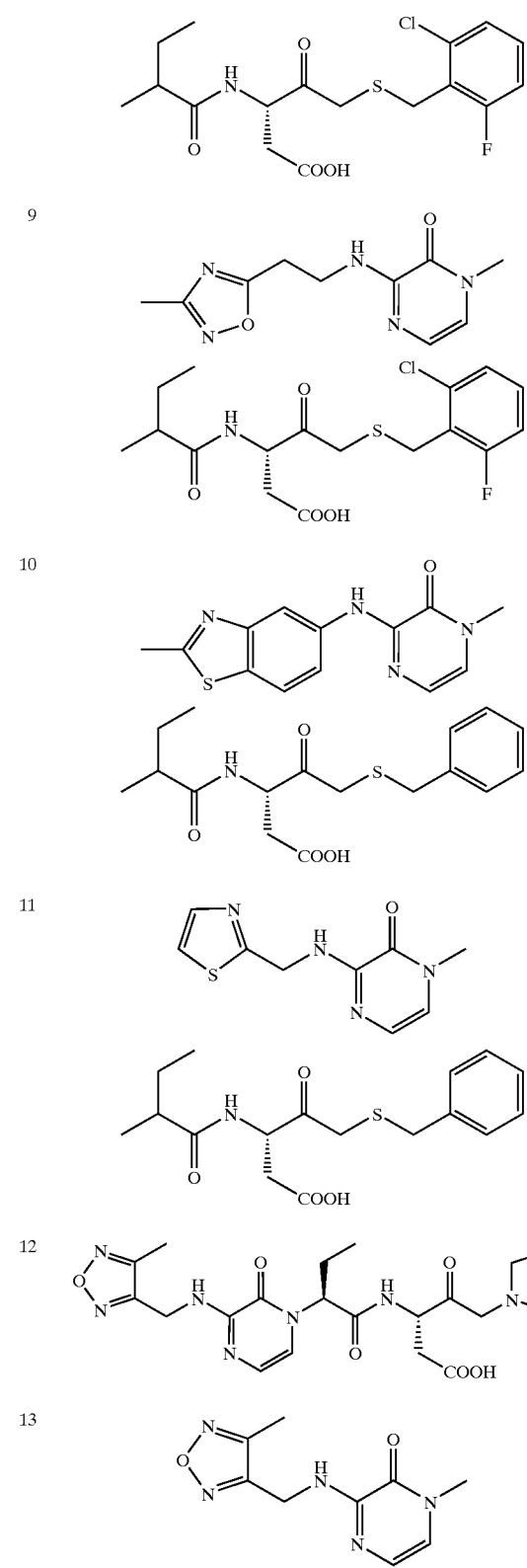
TABLE 1-continued
Compound Number
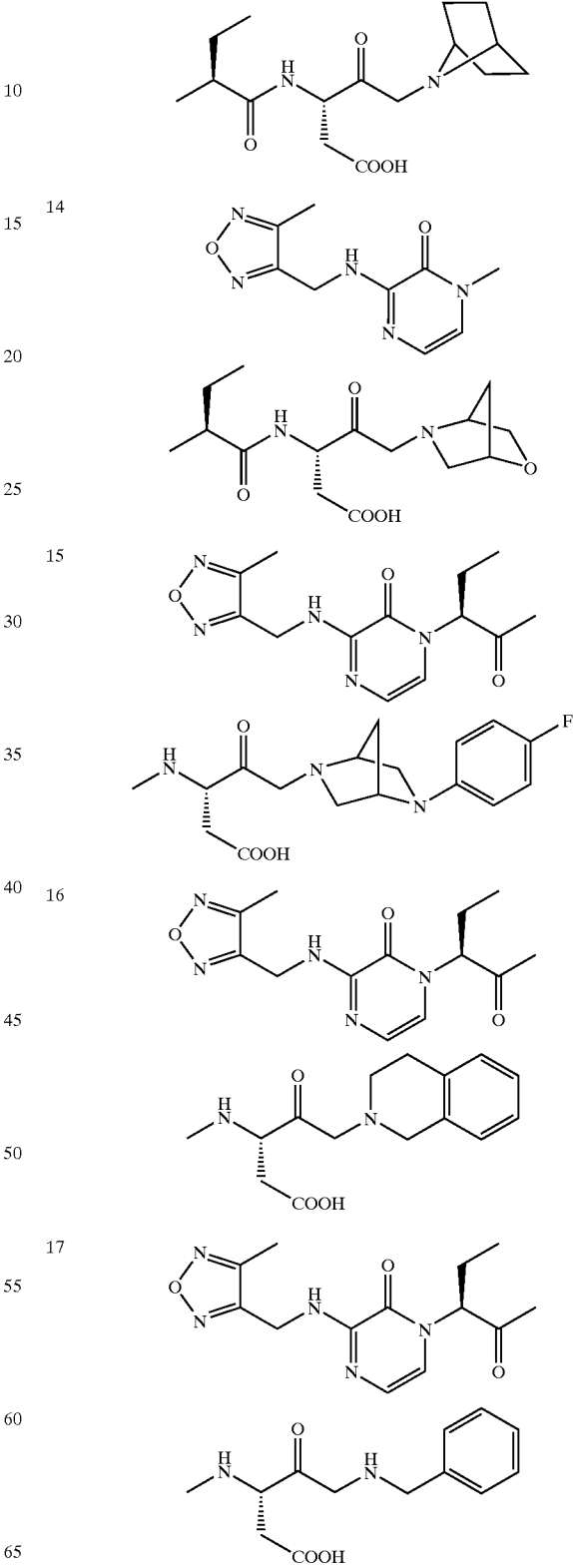

TABLE 1-continued

| Compound Number | Structure |
|---|---|
| 18 | (structure) |
| 19 | (structure) |
| 20 | (structure) |
| 21 | (structure) |
| 22 | (structure) |
| 23 | (structure) |
| 24 | (structure) |
| 25 | (structure) |
| 26 | (structure) |

TABLE 1-continued

| Compound Number | |
|---|---|
| | (structure: N-methylamino, C(=O), CH2-S-benzyl, COOH) |
| 27 | (structure: benzodioxin-CH2-NH-pyrazinone with sec-butyl ketone substituent) |
| | (structure: N-methylamino, C(=O), CH2-S-benzyl, COOH) |
| 28 | (structure: 5-methyl-1,2,4-oxadiazole-CH2-NH-pyrazinone with sec-butyl ketone) |
| | (structure: N-methylamino, C(=O), CH2-S-benzyl, COOH) |
| 29 | (structure: methyl-furazan-CH2-NH-pyrazinone with sec-butyl ketone) |
| | (structure: N-methylamino, C(=O), 5-phenyl-oxazole, COOH) |
| 30 | (structure: methyl-furazan-CH2-NH-pyrazinone-sec-butyl-C(=O)-NH-CH(CH2COOH)-CHO) |

TABLE 1-continued

| Compound Number | |
|---|---|
| 31 | (structure: methyl-furazan-CH2-NH-pyrazinone with ethyl substituent and acetonyl N-substituent) |
| | (structure: N-methylamino, C(=O), CH2-S-(2-chloro-6-fluorobenzyl), COOH) |
| 32 | (structure: methyl-furazan-CH2-NH-pyrazinone with sec-butyl ketone) |
| | (structure: N-methylamino, C(=O), CH2-O-C(=O)-naphthyl, COOH) |
| 33 | (structure: methyl-furazan-CH2-NH-pyrazinone with sec-butyl ketone) |
| | (structure: N-methylamino, C(=O), CH2-N(Me)-benzyl, COOH) |
| 34 | (structure: methyl-furazan-CH2-NH-pyrazinone with sec-butyl ketone) |
| | (structure: N-methylamino, C(=O), CH2-N(Et)-benzyl, COOH) |

TABLE 1-continued

| Compound Number | Structure |
|---|---|
| 35 | (chemical structure) |
| 36 | (chemical structure) |
| 37 | (chemical structure) |
| 38 | (chemical structure) |
| 39 | (chemical structure) |
| 40 | (chemical structure) |
| 41 | (chemical structure) |
| 42 | (chemical structure) |
| 43 | (chemical structure) |
| 44 | (chemical structure) |

TABLE 1-continued

| Compound Number | |
|---|---|
| 45 | (structure) |
| 46 | (structure) |
| 47 | (structure) |
| 48 | (structure) |
| 49 | (structure) |
| 50 | (structure) |
| 51 | (structure) |
| 52 | (structure) |

TABLE 1-continued

| Compound Number | Structure |
|---|---|
| 53 | (chemical structure) |
| 54 | (chemical structure) |
| 55 | (chemical structure) |
| 56 | (chemical structure) |
| 57 | (chemical structure) |
| 58 | (chemical structure) |
| 59 | (chemical structure) |
| 60 | (chemical structure) |

TABLE 1-continued

| Compound Number | Structure |
|---|---|
| 60 | |
| 61 | |
| 62 | |
| 63 | |
| 64 | |
| 65 | |
| 66 | |
| 67 | |
| 68 | |

TABLE 1-continued
| Compound Number | |
|---|---|
| | 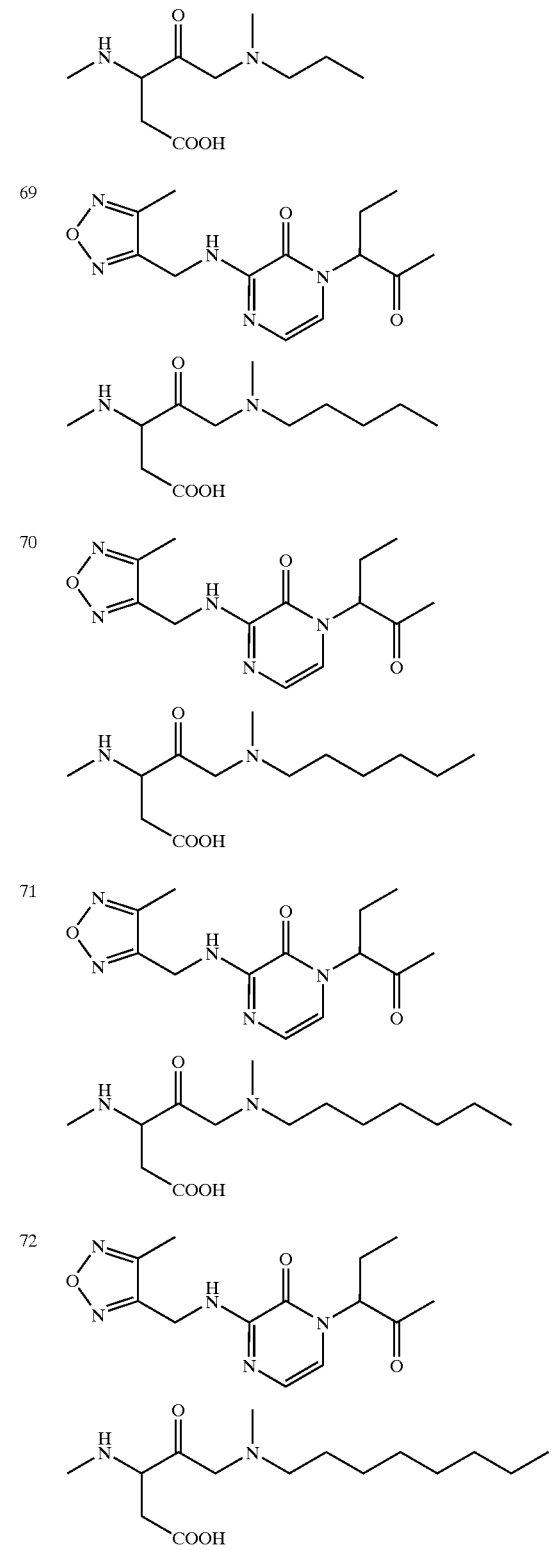 |
TABLE 1-continued
| Compound Number | |
|---|---|
| | 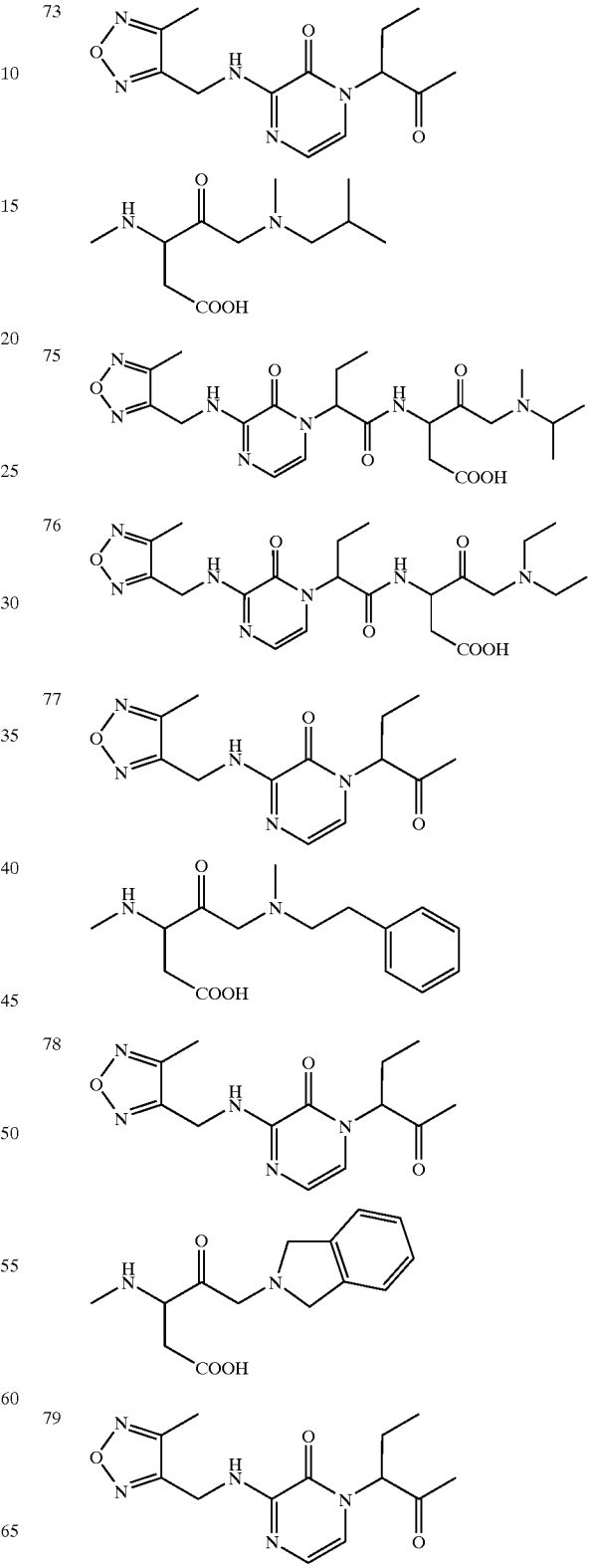 |

TABLE 1-continued
| Compound Number | |
|---|---|
| 80 | 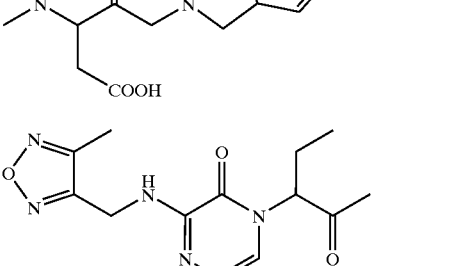 |
| 81 | |
| 82 | |
| 83 | |
| 84 | |
TABLE 1-continued
| Compound Number | |
|---|---|
| 85 | 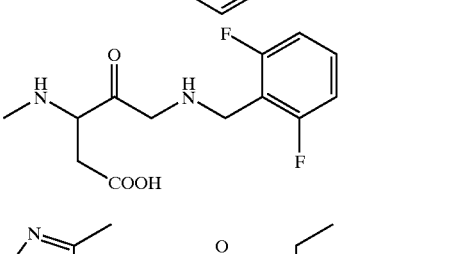 |
| 86 | |
| 87 | |
| 88 | |

TABLE 1-continued

Compound Number 89, 90, 91, 92, 93, 94, 95, 96

TABLE 1-continued

| Compound Number | Structure |
|---|---|
| 97 | (structure) |
| 98 | (structure) |
| 99 | (structure) |
| 100 | (structure) |
| 101 | (structure) |
| 102 | (structure) |
| 103 | (structure) |
| 104 | (structure) |

TABLE 1-continued
| Compound Number | |
|---|---|
| | 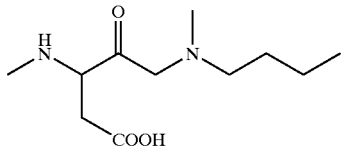 |
| 105 | 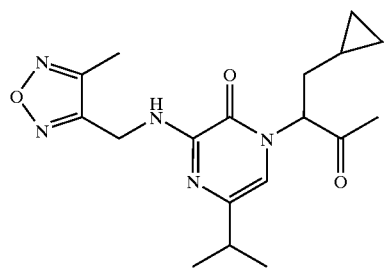 |
TABLE 1-continued
| Compound Number | |
|---|---|
| | 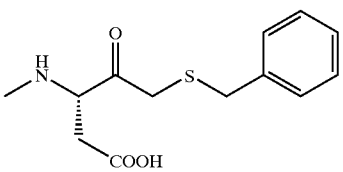 |
or a pharmaceutically acceptable salt, hydrate, N-oxide or ester thereof, said ester formed at the carboxy group shown in the compounds.
* * * * *